US012605201B2

(12) United States Patent

Cappato

(10) Patent No.: US 12,605,201 B2
(45) Date of Patent: *Apr. 21, 2026

(54) SYSTEM, DEVICE, AND METHOD FOR DETERMINING LOCATION OF ARRHYTHMOGENIC FOCI

(71) Applicant: Riccardo Cappato, Milan (IT)

(72) Inventor: Riccardo Cappato, Milan (IT)

( * ) Notice: Subject to any disclaimer, the term of this patent is extended or adjusted under 35 U.S.C. 154(b) by 238 days.

This patent is subject to a terminal disclaimer.

(21) Appl. No.: 17/582,328

(22) Filed: Jan. 24, 2022

(65) Prior Publication Data

US 2023/0117112 A1 Apr. 20, 2023

Related U.S. Application Data

(63) Continuation of application No. 17/505,263, filed on Oct. 19, 2021, now Pat. No. 12,161,396.

(51) Int. Cl.
*A61B 5/287* (2021.01)
*A61B 5/00* (2006.01)
(Continued)

(52) U.S. Cl.
CPC .......... *A61B 18/1492* (2013.01); *A61B 5/287* (2021.01); *A61B 5/361* (2021.01);
(Continued)

(58) Field of Classification Search
CPC ............ A61B 18/1492; A61B 18/1206; A61B 5/0004; A61B 5/0006; A61B 5/0033;
(Continued)

(56) References Cited

U.S. PATENT DOCUMENTS 4,649,924 A 3/1987 Taccardi
4,699,147 A 10/1987 Chilson et al.
(Continued)

FOREIGN PATENT DOCUMENTS

AU 2017276276 12/2017
AU 2019283829 12/2019
(Continued)

OTHER PUBLICATIONS

Invitation to Pay Additional Fees and Annex Communication Relating to the Results of the Partial International Search Issued by the European Patent Office as ISA, on Jan. 25, 2023, in Application Serial No. PCT/IB2022/059700.
(Continued)

*Primary Examiner* — Ronald Hupczey, Jr.
*Assistant Examiner* — Ana Veruska Guerrero
(74) *Attorney, Agent, or Firm* — ROEDER & BRODER LLP; James P. Broder

(57) ABSTRACT

A locator assembly (100) for determining a location of an arrhythmogenic foci (632) in or near a heart (101). The locator assembly (100) includes a device body (112) and a plurality of electrodes (102). The plurality of electrodes (102) receive electrical signals from the heart (101) to determine the location of the arrhythmogenic foci (632). The plurality of electrodes (102) can be coupled to the device body (112). At least two of the plurality of electrodes (102) can positioned circumferentially about the device body (112). The plurality of electrodes (102) can be positionable so that the plurality of electrodes (102) are in electrical communication with the heart (101).

20 Claims, 12 Drawing Sheets

(51) Int. Cl.

| | |
|---|---|
| *A61B 5/318* | (2021.01) |
| *A61B 5/361* | (2021.01) |
| *A61B 5/367* | (2021.01) |
| A61B 18/12 | (2006.01) |
| A61B 18/14 | (2006.01) |
| *A61B 5/0215* | (2006.01) |
| *A61B 5/0245* | (2006.01) |
| *A61B 5/1473* | (2006.01) |
| *A61B 5/28* | (2021.01) |
| *A61B 5/283* | (2021.01) |
| *A61B 5/291* | (2021.01) |
| *A61B 5/308* | (2021.01) |
| *A61B 5/333* | (2021.01) |
| *A61B 18/00* | (2006.01) |
| *A61B 18/18* | (2006.01) |
| *A61B 18/24* | (2006.01) |
| *A61N 1/04* | (2006.01) |
| *A61N 1/368* | (2006.01) |

(52) U.S. Cl.
CPC ............ *A61B 5/367* (2021.01); *A61B 5/6862* (2013.01); *A61B 18/1206* (2013.01); *A61B 5/0004* (2013.01); *A61B 5/0006* (2013.01); *A61B 5/0033* (2013.01); *A61B 5/0036* (2018.08); *A61B 5/004* (2013.01); *A61B 5/0044* (2013.01); *A61B 5/0082* (2013.01); *A61B 5/0084* (2013.01); *A61B 5/0215* (2013.01); *A61B 5/0245* (2013.01); *A61B 5/1473* (2013.01); *A61B 5/28* (2021.01); *A61B 5/283* (2021.01); *A61B 5/291* (2021.01); *A61B 5/308* (2021.01); *A61B 5/318* (2021.01); *A61B 5/333* (2021.01); *A61B 5/6867* (2013.01); *A61B 5/6869* (2013.01); *A61B 2018/00214* (2013.01); *A61B 2018/0022* (2013.01); *A61B 2018/00279* (2013.01); *A61B 2018/00285* (2013.01); *A61B 2018/00345* (2013.01); *A61B 2018/00351* (2013.01); *A61B 2018/00369* (2013.01); *A61B 2018/1226* (2013.01); *A61B 2018/1246* (2013.01); *A61B 2018/126* (2013.01); *A61B 2018/183* (2013.01); *A61B 18/24* (2013.01); *A61B 2560/0462* (2013.01); *A61B 2560/0468* (2013.01); *A61B 2560/063* (2013.01); *A61B 2560/066* (2013.01); *A61N 1/04* (2013.01); *A61N 1/0416* (2013.01); *A61N 1/3684* (2013.01)

(58) Field of Classification Search
CPC ..... A61B 5/0036; A61B 5/004; A61B 5/0044; A61B 5/0082; A61B 5/0084; A61B 5/0215; A61B 5/0245; A61B 5/1473; A61B 5/28; A61B 5/283; A61B 5/291; A61B 5/308; A61B 5/318; A61B 5/333; A61B 5/6867; A61B 5/6869; A61B 18/24; A61B 2018/00214; A61B 2018/0022; A61B 2018/00279; A61B 2018/00285; A61B 2018/00351; A61B 2018/00369; A61B 2018/1226; A61B 2018/1246; A61B 2018/126; A61B 2018/183; A61B 2560/0462; A61B 2560/0468; A61B 2560/063; A61B 2560/066; A61B 5/287; A61B 5/367; A61B 5/6862; A61N 1/04; A61N 1/0416; A61N 1/3684; A61N 1/362
See application file for complete search history.

(56) References Cited

U.S. PATENT DOCUMENTS

| | | | |
|---|---|---|---|
| 5,697,377 A | 12/1997 | Wittkampf | |
| 5,718,241 A | 2/1998 | Ben-Haim et al. | |
| 6,500,174 B1 | 12/2002 | Maguire et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 8,364,235 B2 | 1/2013 | Kordis et al. | |
| 8,644,927 B2 | 2/2014 | Imran | |
| 9,119,533 B2 | 9/2015 | Ghaffari | |
| 9,138,160 B2 | 9/2015 | Imran | |
| 9,289,132 B2 | 3/2016 | Ghaffari et al. | |
| 9,629,567 B2 | 4/2017 | Porath et al. | |
| 9,662,069 B2 | 5/2017 | De Graff et al. | |
| 9,687,166 B2 | 6/2017 | Subramaniam et al. | |
| 9,764,142 B2 | 9/2017 | Imran | |
| 9,861,433 B2* | 1/2018 | Tegg ................ A61M 25/0012 |
| 9,894,756 B2 | 2/2018 | Weinkam et al. | |
| 9,974,963 B2 | 5/2018 | Imran | |
| 9,974,970 B2* | 5/2018 | Nuta .................. A61N 1/39622 |
| 10,136,829 B2* | 11/2018 | Deno ..................... A61B 5/316 |
| 10,194,994 B2 | 2/2019 | Deno et al. | |
| 10,537,287 B2 | 1/2020 | Braido et al. | |
| 10,549,092 B1 | 2/2020 | Hakki | |
| 10,575,783 B2 | 3/2020 | Oxley | |
| 10,722,240 B1* | 7/2020 | Melanson ........ A61B 17/12122 |
| 10,894,167 B2 | 1/2021 | Koop et al. | |
| 11,013,554 B2* | 5/2021 | Coates .............. A61B 18/0206 |
| 11,093,038 B2 | 8/2021 | Yoo | |
| 11,550,391 B2 | 1/2023 | Yoo et al. | |
| 11,625,014 B2 | 4/2023 | Oxley et al. | |
| 11,630,517 B1 | 4/2023 | Yoo et al. | |
| 11,672,986 B2 | 6/2023 | Opie et al. | |
| 11,755,110 B2 | 9/2023 | Yoo | |
| 11,883,671 B2 | 1/2024 | Opie et al. | |
| 2003/0050637 A1* | 3/2003 | Maguire ................. A61N 7/02 |
| | | | 606/41 |
| 2003/0176816 A1 | 9/2003 | Maguire | |
| 2005/0010095 A1 | 1/2005 | Stewart et al. | |
| 2005/0273014 A1 | 12/2005 | Gianchandani et al. | |
| 2005/0277839 A1 | 12/2005 | Alderman et al. | |
| 2006/0200039 A1 | 9/2006 | Brockway et al. | |
| 2006/0241733 A1 | 10/2006 | Zhang et al. | |
| 2008/0039904 A1 | 2/2008 | Bulkes | |
| 2008/0077184 A1 | 3/2008 | Denker | |
| 2009/0192405 A1 | 7/2009 | Carney | |
| 2009/0192495 A1 | 7/2009 | Ostrovsky et al. | |
| 2010/0063562 A1 | 3/2010 | Cowan | |
| 2010/0179632 A1 | 7/2010 | Bruszewski et al. | |
| 2010/0191089 A1 | 7/2010 | Stebler et al. | |
| 2012/0197150 A1 | 8/2012 | Cao et al. | |
| 2013/0253347 A1 | 9/2013 | Griswold et al. | |
| 2014/0288667 A1 | 9/2014 | Oxley | |
| 2015/0065945 A1* | 3/2015 | Zarins .................... A61B 18/04 |
| | | | 514/183 |
| 2015/0141764 A1 | 5/2015 | Harks et al. | |
| 2016/0038087 A1 | 2/2016 | Hunter | |
| 2016/0235999 A1 | 8/2016 | Nuta | |
| 2016/0287174 A1* | 10/2016 | Joseph ................... A61B 5/686 |
| 2016/0351292 A1 | 12/2016 | Toth | |
| 2017/0042615 A1* | 2/2017 | Salahieh .................. A61B 5/01 |
| 2018/0049877 A1 | 2/2018 | Venkatasubramanian | |
| 2018/0092763 A1 | 4/2018 | Dagan et al. | |
| 2018/0132754 A1 | 5/2018 | Kusumoto | |
| 2018/0272121 A1 | 9/2018 | Yankelson | |
| 2019/0175111 A1 | 6/2019 | Genereux et al. | |
| 2019/0175372 A1 | 6/2019 | Boyden et al. | |
| 2019/0232066 A1 | 8/2019 | Lim et al. | |
| 2019/0328259 A1 | 10/2019 | Deno | |
| 2019/0388002 A1 | 12/2019 | Bozsak et al. | |
| 2020/0016396 A1 | 1/2020 | Yoo | |
| 2020/0363869 A1 | 11/2020 | Yoo | |
| 2021/0373665 A1 | 12/2021 | Yoo | |
| 2021/0378595 A1 | 12/2021 | Oxley | |
| 2022/0039730 A1 | 2/2022 | Ravuna et al. | |
| 2022/0240833 A1 | 8/2022 | Oxley | |

</div>

(56) References Cited

U.S. PATENT DOCUMENTS

| | | | |
|---|---|---|---|
| 2022/0253024 A1 | 8/2022 | Oxley et al. | |
| 2022/0369994 A1 | 11/2022 | Oxley | |
| 2023/0101497 A1 | 3/2023 | Werneth | |
| 2023/0107850 A1 | 4/2023 | Yoo et al. | |
| 2023/0121587 A1 | 4/2023 | Cappato | |
| 2023/0218198 A1 | 7/2023 | Bennett et al. | |
| 2023/0244314 A1 | 8/2023 | Oxley et al. | |
| 2023/0288987 A1 | 9/2023 | Yoo et al. | |
| 2023/0302282 A1 | 9/2023 | Opie et al. | |
| 2023/0350360 A1 | 11/2023 | Oxley et al. | |
| 2023/0389851 A1 | 12/2023 | Tal et al. | |
| 2024/0019933 A1 | 1/2024 | Yoo | |
| 2025/0319317 A1 | 10/2025 | Cappato | |

FOREIGN PATENT DOCUMENTS

| | | | | |
|---|---|---|---|---|
| CA | 3144083 | 11/2020 | | |
| CN | 104023787 | 7/2017 | | |
| CN | 107374623 | 11/2017 | | |
| CN | 114144748 | 3/2022 | | |
| CN | 115052657 | 9/2022 | | |
| CN | 115698906 | 2/2023 | | |
| EP | 3536375 | 11/2019 | | |
| EP | 3576618 A1 | 12/2019 | | |
| JP | A2006130064 | 5/2006 | | |
| JP | A2008237882 | 10/2008 | | |
| JP | 6149269 | 6/2017 | | |
| JP | 2017159079 | 9/2017 | | |
| JP | A2020529879 | 10/2020 | | |
| JP | A2021505353 | 2/2021 | | |
| JP | A2021069921 | 5/2021 | | |
| JP | 2022533090 | 7/2022 | | |
| JP | 2023501446 | 1/2023 | | |
| JP | 2023519968 | 5/2023 | | |
| KR | 20160090877 A | 8/2016 | | |
| KR | 20220030935 | 3/2022 | | |
| KR | 20230019403 | 2/2023 | | |
| WO | WO 2000069334 A1 * | 5/2000 | ............ | A61B 5/287 |
| WO | WO-0069334 A1 * | 11/2000 | ............ | A61B 5/287 |
| WO | WO-2007137077 A2 * | 11/2007 | ......... | A61B 5/04012 |
| WO | WO2010042653 A1 | 4/2010 | | |
| WO | WO2012025245 A1 | 3/2012 | | |
| WO | WO2013049887 A1 | 4/2013 | | |
| WO | WO2014177634 A1 | 11/2014 | | |
| WO | WO2017070252 A1 | 4/2017 | | |
| WO | WO2018185256 A1 | 10/2018 | | |
| WO | WO2020227774 | 11/2020 | | |
| WO | WO2021086972 | 5/2021 | | |
| WO | WO2021092462 | 5/2021 | | |
| WO | WO2021097448 | 5/2021 | | |
| WO | WO2021202915 | 10/2021 | | |
| WO | WO2023137396 | 7/2023 | | |
| WO | WO2023137427 | 7/2023 | | |
| WO | WO2023147233 | 8/2023 | | |
| WO | WO2023240043 | 12/2023 | | |
| WO | WO2024006998 | 1/2024 | | |
| WO | WO2025215590 A1 | 10/2025 | | |

OTHER PUBLICATIONS

Gardner J., "Moving with the Power of Thought", https://pursuit.unimelb.edu.au/articles/moving-with-the-power-of-thought. Feb. 9, 2016.

Hodsen, S., "DARPA: Minimally Invasive Implant Could Unlock Thought-Controlled Prosthetics", https://www.meddeviceonline.com/doc/darpa-minimally-invasive-implant-could-unlock-thought-controlled-prosthetics-0001. Feb. 24, 2016.

Synchron https://synchron.com/ accessed on Oct. 17, 2022.

Nademanee, K., M.D., Faac, et al., "A New Approach For Catheter Ablation of Atrial Fibrillation: Mapping of the Electrophysiologic Substrate". Journal of the American College of Cardiology, 2004, vol. 43, No. 11.

Meng, S., et al., "Accurate recovery of atrial endocardial potential maps from non-contact electrode data". Auckland Bioengineering Institute, The University of Auckland, New Zealand.

Shariat, M.H., et al. "Localization of the Ectopic Spiral Electrial Source Using Intracardiac Electrograms During Atrial Fibrillation". Proceeding of the IEEE 28th, Canadian Conference on Electrical and Computer Engineering, Halifax, Canada, May 3-6, 2015.

Jiang, R., MD., et al., "Multielectrode Catheter for Substrate Mapping for Scar-Related VT Ablation: A Comparison between Grid versus Linear Configurations". At the Forefront UChicago Medicine; Center for Arrhythmia Care; Heart and Vascular Center; Chicago, IL.

Calkins, H., "Three Dimensional Mapping of Atrial Fibrillation: Techniques and Necessity". Journal of Interventional Cardiac Electrophysiology 13, 53-59, 2005.

Shariat, M.H., "Processing the Intracardiac Electrogram for Atrial Fibrillation Ablation". Queen's University, Kingston, Ontario, Canada, Sep. 2016.

Sacher, F., et al. "Comparison of Manual vs. Automatic Annotation to Identify Abnormal Substrate for Scar Related VT Ablation". CHU, University of Bordeaux.

"Reveal LINQ LNQ11, Insertable Cardiac Monitor", Clinician Manual. Medtronic, Inc. 2015.

International Search Report and Written Opinion, issued by ISA European Patent Office, Aug. 4, 2025, in Application Serial No. PCT/IB2025/053801.

* cited by examiner

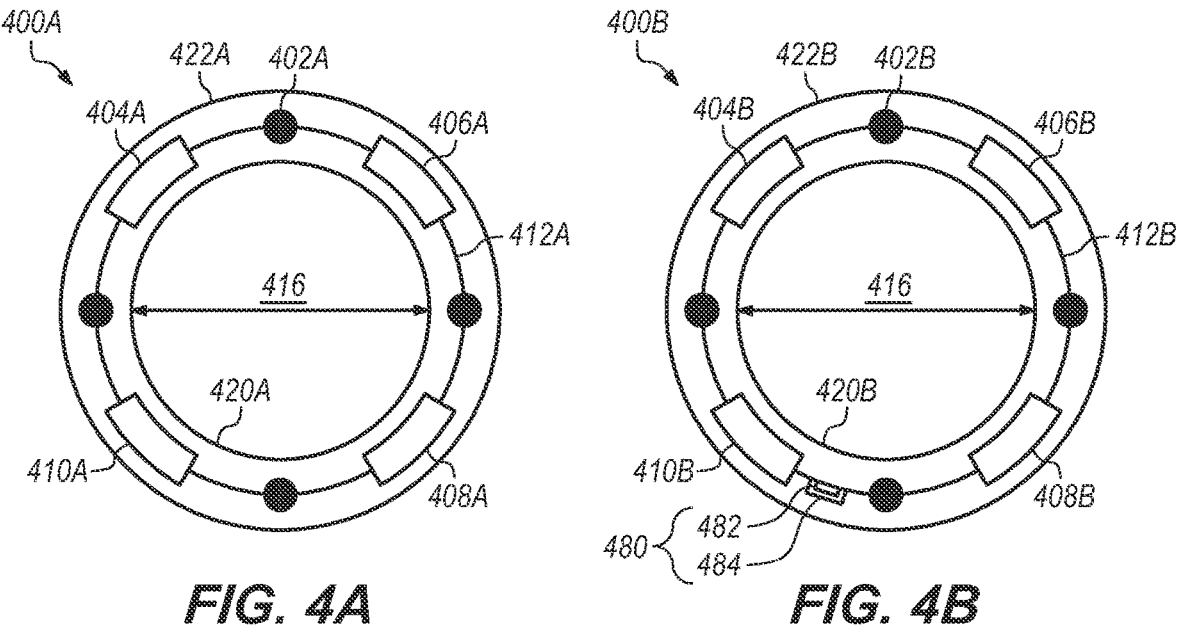
FIG. 4A                                    FIG. 4B
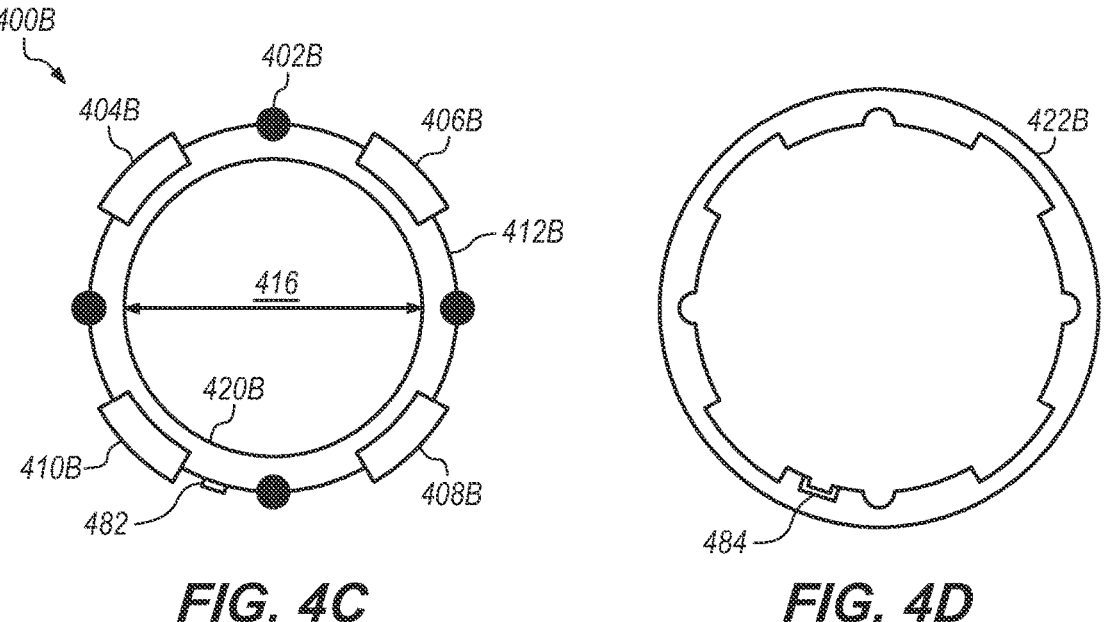
FIG. 4C                                    FIG. 4D

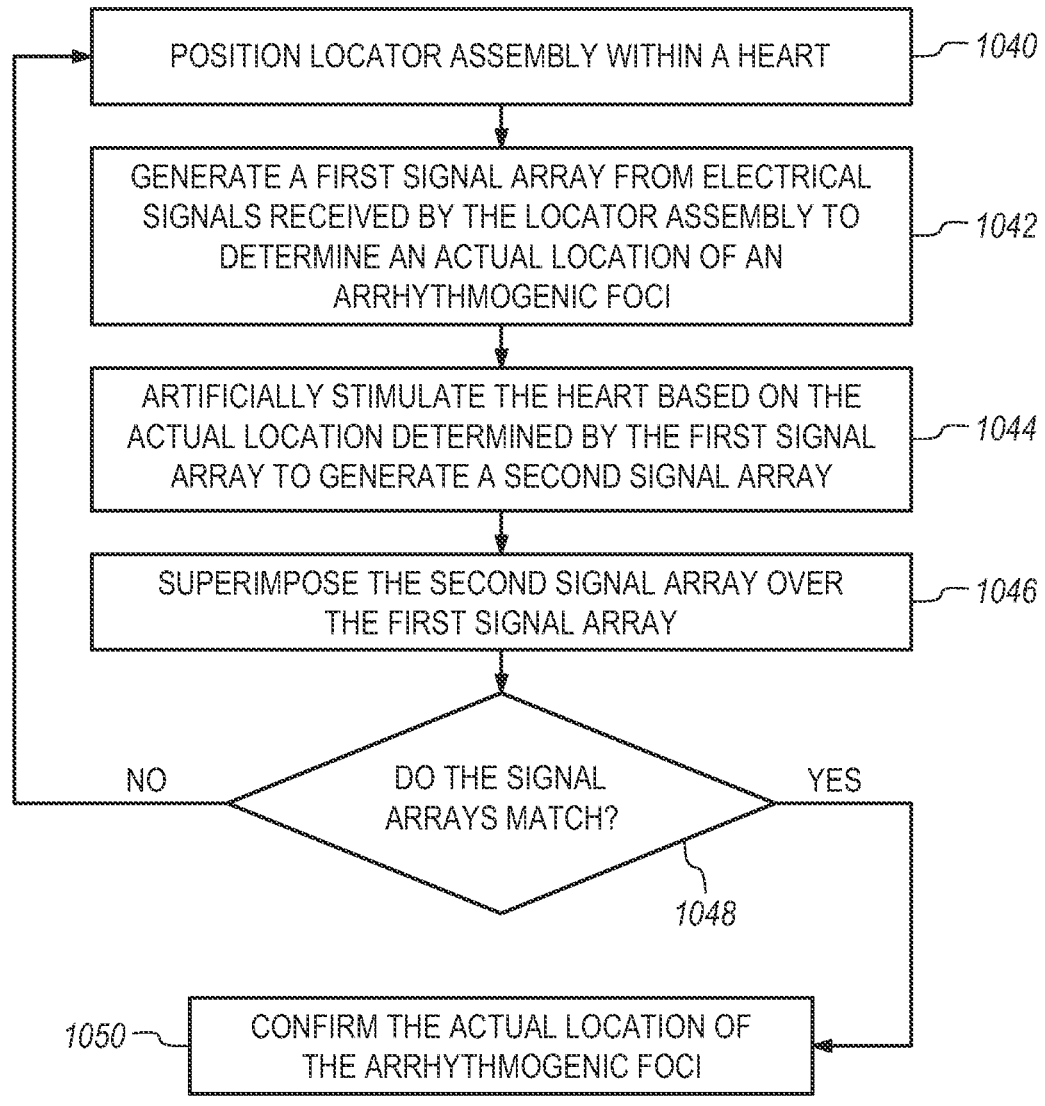

POSITION LOCATOR ASSEMBLY WITHIN A HEART          1040

GENERATE A FIRST SIGNAL ARRAY FROM ELECTRICAL SIGNALS RECEIVED BY THE LOCATOR ASSEMBLY TO DETERMINE AN ACTUAL LOCATION OF AN ARRHYTHMOGENIC FOCI          1042

ARTIFICIALLY STIMULATE THE HEART BASED ON THE ACTUAL LOCATION DETERMINED BY THE FIRST SIGNAL ARRAY TO GENERATE A SECOND SIGNAL ARRAY          1044

SUPERIMPOSE THE SECOND SIGNAL ARRAY OVER THE FIRST SIGNAL ARRAY          1046

NO          DO THE SIGNAL ARRAYS MATCH?          YES
1048

1050          CONFIRM THE ACTUAL LOCATION OF THE ARRHYTHMOGENIC FOCI

FIG. 10

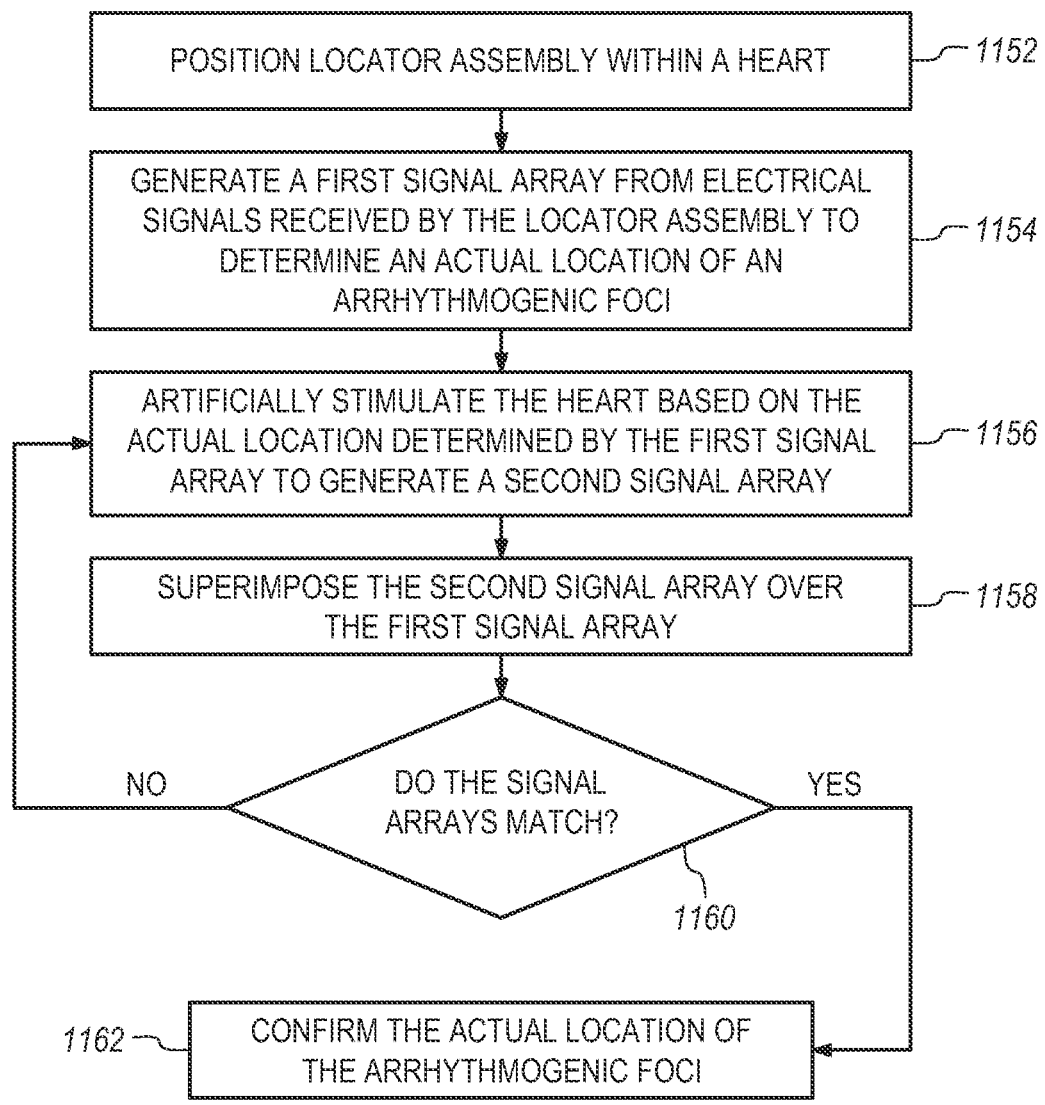

POSITION LOCATOR ASSEMBLY WITHIN A HEART — 1152

GENERATE A FIRST SIGNAL ARRAY FROM ELECTRICAL SIGNALS RECEIVED BY THE LOCATOR ASSEMBLY TO DETERMINE AN ACTUAL LOCATION OF AN ARRHYTHMOGENIC FOCI — 1154

ARTIFICIALLY STIMULATE THE HEART BASED ON THE ACTUAL LOCATION DETERMINED BY THE FIRST SIGNAL ARRAY TO GENERATE A SECOND SIGNAL ARRAY — 1156

SUPERIMPOSE THE SECOND SIGNAL ARRAY OVER THE FIRST SIGNAL ARRAY — 1158

NO     DO THE SIGNAL ARRAYS MATCH?     YES     1160

1162 — CONFIRM THE ACTUAL LOCATION OF THE ARRHYTHMOGENIC FOCI

*FIG. 11*

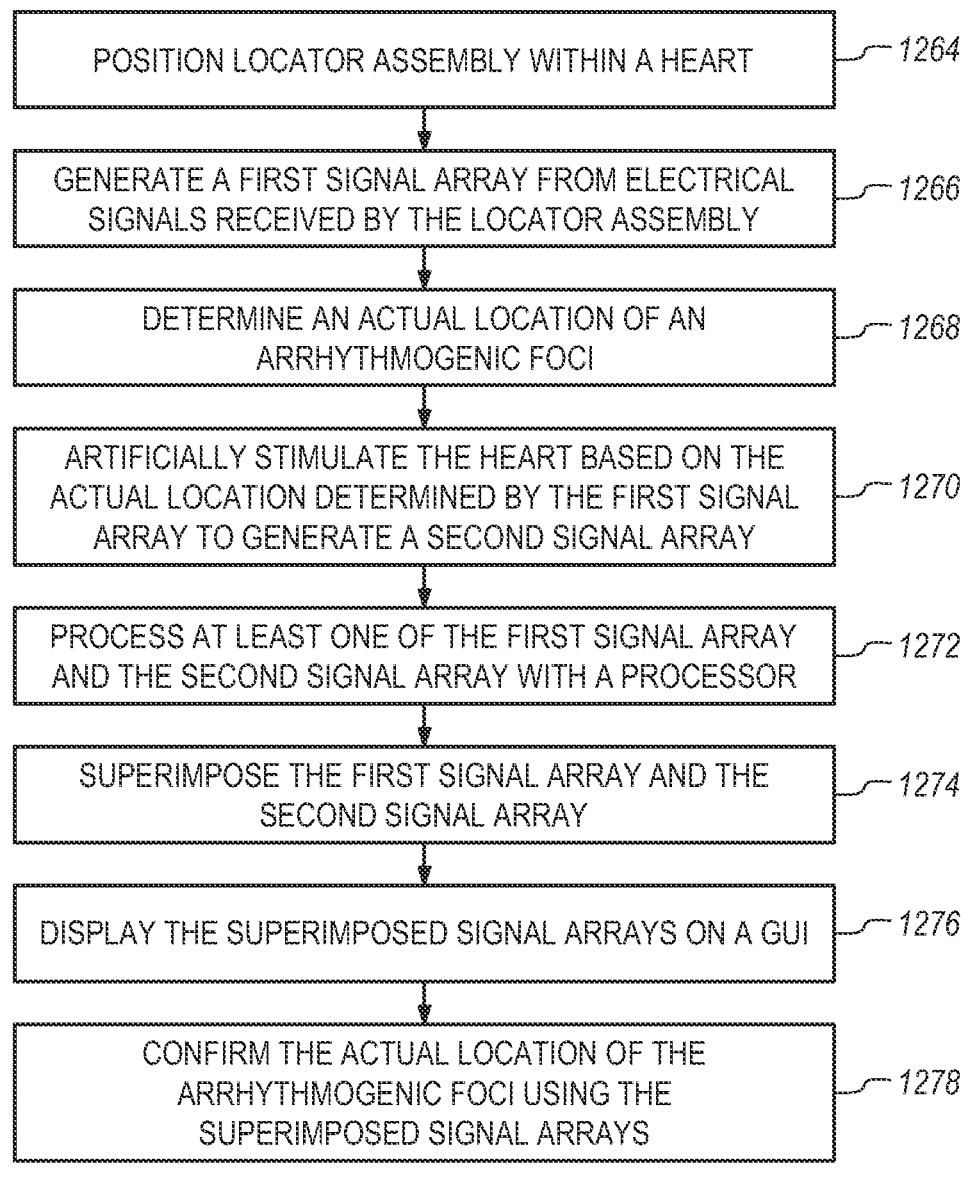

POSITION LOCATOR ASSEMBLY WITHIN A HEART — 1264

GENERATE A FIRST SIGNAL ARRAY FROM ELECTRICAL SIGNALS RECEIVED BY THE LOCATOR ASSEMBLY — 1266

DETERMINE AN ACTUAL LOCATION OF AN ARRHYTHMOGENIC FOCI — 1268

ARTIFICIALLY STIMULATE THE HEART BASED ON THE ACTUAL LOCATION DETERMINED BY THE FIRST SIGNAL ARRAY TO GENERATE A SECOND SIGNAL ARRAY — 1270

PROCESS AT LEAST ONE OF THE FIRST SIGNAL ARRAY AND THE SECOND SIGNAL ARRAY WITH A PROCESSOR — 1272

SUPERIMPOSE THE FIRST SIGNAL ARRAY AND THE SECOND SIGNAL ARRAY — 1274

DISPLAY THE SUPERIMPOSED SIGNAL ARRAYS ON A GUI — 1276

CONFIRM THE ACTUAL LOCATION OF THE ARRHYTHMOGENIC FOCI USING THE SUPERIMPOSED SIGNAL ARRAYS — 1278

*FIG. 12*

SYSTEM, DEVICE, AND METHOD FOR DETERMINING LOCATION OF ARRHYTHMOGENIC FOCI

RELATED APPLICATION

This continuation application claims priority on U.S. application Ser. No. 17/505,263, filed on Oct. 19, 2021, and entitled "SYSTEM, DEVICE, AND METHOD FOR DETERMINING LOCATION OF ARRHYTHMOGENIC FOCI". As far as permitted, the contents of U.S. application Ser. No. 17/505,263 are incorporated in their entirety herein by reference.

BACKGROUND

Atrial fibrillation is an irregular and sometimes rapid heart rate that can increase the risk of stroke, heart failure, and other heart-related complications. During atrial fibrillation, the heart's two upper chambers (the atria) beat chaotically and irregularly—out of coordination with the heart's two lower chambers (the ventricles). Atrial fibrillation symptoms often include heart palpitations, shortness of breath, and weakness. Although atrial fibrillation usually isn't life-threatening, it is a severe medical condition that sometimes requires treatment. Atrial fibrillation can originate from focal sources (referred to herein as "arrhythmogenic foci") in the atria or other locations in and around the heart.

Catheter ablation of atrial fibrillation is currently performed using an anatomically-based approach to the atrial substrate. Previous models hypothesize that most clinical atrial fibrillation episodes originate inside the pulmonary veins. Eligible patients for atrial fibrillation ablation are not representative of the typical patient with atrial fibrillation (e.g., eligible patients for atrial fibrillation ablation on average are ten years younger, commonly with fewer co-morbidities). As a result, pulmonary vein isolation is unlikely to be an effective strategy to cure atrial fibrillation in the overall population of atrial fibrillation patients.

The anatomically-based approach to the atrial substrate surrogates the ability of clinicians to provide relevant electrophysiological information during clinical episodes of atrial fibrillation. Problems with the anatomically-based approach include (1) recurrent conduction across the isolating ablation lesions deployed at the pulmonary vein orifice/antrum, (2) precipitation of atrial fibrillation events from sites other than the pulmonary vein. Recurrence of atrial fibrillation events includes many patients among those in whom pulmonary vein isolation fails to control recurrences of atrial fibrillation. In all patients with previously successful pulmonary vein isolation, recurrent episodes still exist.

Mapping areas alternative to pulmonary veins that generate extra beats precipitating atrial fibrillation episodes is currently precluded by the inability to monitor real-time precipitating episodes. Other approaches, such as a surrogate strategy to real-time mapping, are represented by catecholamine-induced atrial fibrillation during ablation procedures. However, the surrogate strategy is not standardized, is time-consuming and ineffective (drug-induced atrial fibrillation does not represent spontaneous atrial fibrillation). Another major problem is the ability to accurately determine the precise location of the arrhythmogenic foci that is causing atrial fibrillation.

SUMMARY

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 4A is a simplified end view of an embodiment of the locator assembly;

FIG. 4B is a simplified end view of yet another embodiment of the locator assembly;

FIG. 4C is a simplified end view of a portion of the embodiment of the locator assembly shown in FIG. 4B;

FIG. 4D is a simplified end view of yet another portion of the embodiment of the locator assembly shown in FIG. 4B;

FIG. 10 is a flow chart outlining one embodiment of a method for determining the location of arrhythmogenic foci in the heart;

FIG. 11 is a flow chart outlining another embodiment of a method for determining the location of arrhythmogenic foci in the heart; and FIG. 12 is a flow chart outlining yet another embodiment of a method for determining the location of arrhythmogenic foci in the heart.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

The systems, devices, and related methods for determining the location of arrhythmogenic foci are configured to enable mapping of precipitating episodes of clinical atrial fibrillation during a patient's daily life. In particular, a locator assembly 100 can be implanted within the patient so that the locator assembly 100 can locate the origin of clinical atrial fibrillation in or near a heart 101 of the patient. As used herein, the "heart" is understood to mean the heart including both atrial chambers, both ventricular chambers, the septum, the pulmonary veins, the coronary sinus, the fossa ovalis, the superior vena cava, the inferior vena cava, the muscular sleeves, the vascular walls, connected, electrically active tissues, and all other heart support structures in or near the heart.

The locator assembly 100 can be used in the systems and methods described herein for determining a location of an arrhythmogenic foci 632 (illustrated in FIG. 6, for example) in or near the heart 101 of the patient. The systems, methods, and devices for determining the location of the arrhythmogenic foci 632 in or near the heart 101 described herein can vary.

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention, as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming but would nevertheless be a routine undertaking of engineering for those of ordinary skill in the art having the benefit of this disclosure.

Figure 1A:
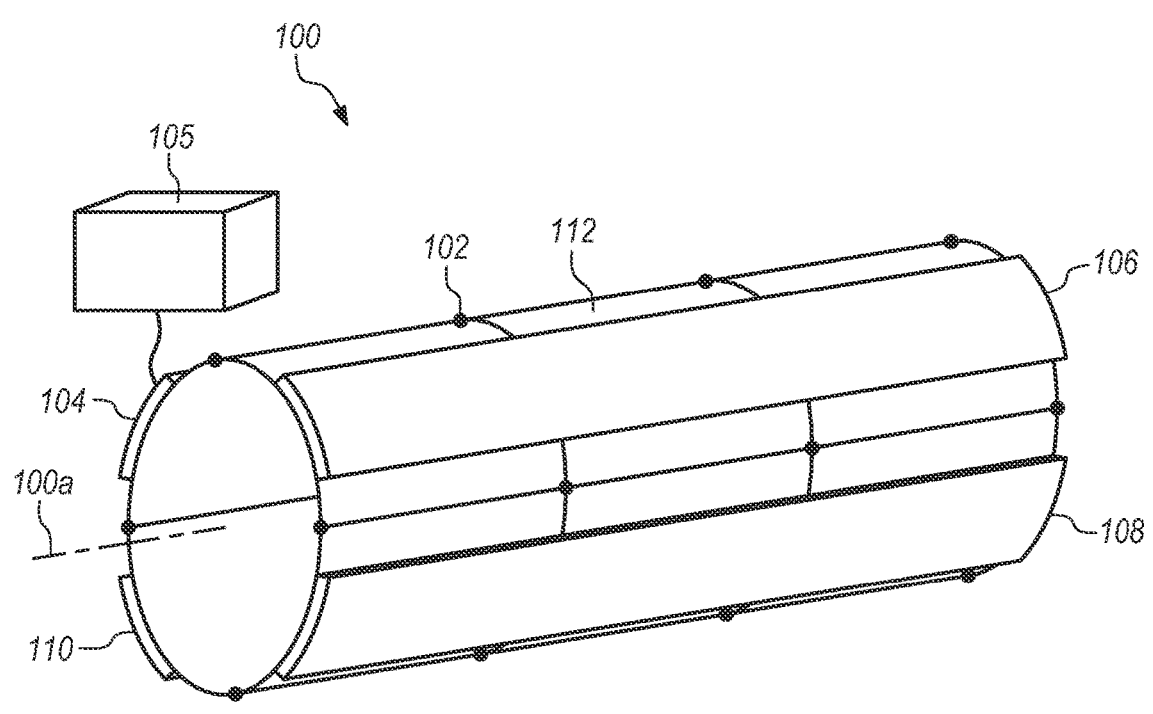
FIG. 1A is a simplified perspective view of an embodiment of a locator assembly for locating an arrhythmogenic foci in or near a heart and an external device, the locator assembly having features of the present invention.

FIG. 1A is a simplified perspective view of an embodiment of a locator assembly 100 for locating arrhythmogenic foci 632 (illustrated in FIG. 6) in or near the heart 101, and an external device 105. As provided herein, the locator assembly 100 is deliverable to a portion of the heart 101 of a patient. The locator assembly 100 can map precipitating episodes of clinical atrial fibrillation during the patient's daily life. The locator assembly 100 can be expandable to become anchored in a portion of the heart 101 of the patient.

In various embodiments, the locator assembly 100 can be configured to provide cardiac telemetry monitoring and sampling of electrophysiological signals from the heart 101 of the patient. It is appreciated that, by providing the locator assembly 100 with telemetry capabilities, the locator assembly 100 can be more suitable for patients with asymptomatic, rare, or intermittent atrial fibrillation episodes.

In one embodiment, the locator assembly 100 can sample electrocardiogram signals from the heart 101 of the patient periodically (in either even or uneven time increments) throughout a sampling period. In some embodiments, the sampling period can be between one hour and one year. In other embodiments, the sampling period can be less than one hour or greater than one year. The locator assembly 100 can capture an arrhythmia or an arrhythmogenic foci 632 that may not be captured during a shorter sampling period by providing more extended sampling periods.

In certain embodiments, the locator assembly 100 is positioned and expanded within the heart 101 of the patient. In some embodiments, the locator assembly 100 can operate somewhat similarly to an expandable stent. The locator assembly 100 can be placed within the patient permanently. Alternatively, the locator assembly 100 can be removed from the patient, such as after the locator assembly 100 runs out of stored power, to replace or repair various components, or for any other suitable purpose. The locator assembly 100 has a longitudinal axis 100a but may also have other axes. The locator assembly 100 has a circumference 100c.

In some embodiments, if the cross-section of the locator assembly 100 is a perfect circle and the longitudinal axis 100a is perfectly centered through the end of the locator assembly 100, all positions on the circumference 100c are equidistant from the longitudinal axis 100a. In various embodiments, the locator assembly 100 and its incorporated elements and components thereof can be rechargeable. In one embodiment, the locator assembly 100 can be wirelessly recharged while the locator assembly 100 is positioned within the patient.

The locator assembly 100 can vary depending on its design requirements. It is understood that the locator assembly 100 can include additional components, systems, subsystems, and elements other than those specifically shown and/or described herein. Additionally, or alternatively, the locator assembly 100 can omit one or more of the components, systems, subsystems, and elements that are specifically shown and/or described herein. In some embodiments, various components of the locator assembly 100 can be positioned in a different manner than what is specifically illustrated in FIG. 1A. In some embodiments, the locator assembly 100 can have the same or a somewhat similar design to a bare-metal stent, as one non-limiting, non-exclusive example.

Components of the locator assembly 100 can be configured to operate for a finite period or an average lifespan of the patient, if not longer. If necessary, some or all of the components and/or elements of the locator assembly 100 could potentially become immobilized during the extraction and/or replacement of the locator assembly 100.

In the embodiment illustrated in FIG. 1A, the locator assembly 100 can include a plurality of electrodes 102 (only one electrode is identified, with other electrodes shown as black dots in FIG. 1A, FIGS. 2A-2B, and FIGS. 3-4), a communicator 104, a controller 106, a routing layer 108, a battery 110, and a device body 112. As used herein, the "components" of the locator assembly 100 can include the plurality of electrodes 102, the communicator 104, the controller 106, the routing layer 108, and the battery 110.

In various embodiments, the locator assembly 100 can be configured for use by the patient while the patient receives a magnetic resonance imaging scan, or other imaging procedures. In other words, the locator assembly 100 can have shielding and/or resistance to varying types of external electromagnetic radiation. In some embodiments, the locator assembly 100 can be automatically activated and/or powered on. In certain embodiments, the locator assembly 100 can be manually activated and/or powered on by the patient or a health care personnel.

As shown in FIG. 1A, the components of the locator assembly 100, such as the electrodes 102, the communicator 104, the controller 106, the routing layer 108, and the battery 110, can be radially spaced apart from one another about the circumference 100c. For example, in various non-exclusive embodiments, the components of the locator assembly 100 can be spaced apart by 1, 5, 10, 15, 20, 25, 30, 35, 40, 45, 60, 90, 120, or 180 degrees about the circumference 100c. In other embodiments, the components of the locator assembly 100 can be spaced apart by less than 1 degree or some other radial spacing other than those listed herein.

The components of the locator assembly 100 can be positioned as provided above, even if the cross-sectional shape of the locator assembly 100 is something other than a circle. The cross-sectional shape of the locator assembly 100 can be any suitable shape. Non-limiting, non-exclusive examples of the cross-sectional shape of the locator assembly 100 include circular-shaped, oval-shaped, egg-shaped, pentagonal-shaped, hexagonal-shaped, heptagonal-shaped, octagonal-shaped, decagonal-shaped, or any suitable shape. The cross-sectional shape of the locator assembly 100 can have any number of sides and any type of curvature.

In some embodiments, the components of the locator assembly 100 can be spaced apart substantially equidistant from each other about the circumference 100c. The locator assembly 100 can include a plurality of platforms (not shown) configured to retain corresponding components of the locator assembly 100 about the circumference 100c. In other embodiments, such as shown in FIG. 1, the components of the locator assembly 100 can integrate platforms configured to enable coupling to the locator assembly 100.

The electrodes 102 record and sense electrical signals (such as electrophysiological signals) sent from the heart 101 and nearby portions of the body. In some embodiments, the electrodes 102 can record the atrial activity and related electrical impulses.

The type of electrodes 102 can vary depending on the design requirements of the locator assembly 100. In some embodiments, the electrode 102 can be positioned in different configurations than what is specifically illustrated in FIG. 1A.

The electrodes 102 can include any suitable types of electrodes, including one or more electrocardiogram electrodes (as a non-limiting, non-exclusive example). The electrodes 102, when positioned in pairs, can form bipolar electrodes. The electrodes 102 can be coupled and decoupled from the locator assembly 100 to repair or replace defective or otherwise inoperable electrodes 102 of the locator assembly 100. The locator assembly can include any suitable number of electrodes 102. In some embodiments, such as FIG. 1A, the locator assembly 100 can include 16 electrodes 102. In other embodiments, the locator assembly 100 can include 2, 4, 6, 8, 10, 12, 14, 16, 18, 20, 22, 24, 26, 28, 30, or 32 electrodes 102. In certain embodiments, the locator assembly can 100 can include greater than 32 electrodes.

The electrodes 102 can be distributed about the circumference 100c in a pattern, either in the longitudinal and/or circumferential directions or on any suitable portion of the locator assembly 100. About the circumference 100c of the locator assembly 100, the electrodes 102 can be spaced apart by 10, 20, 30, 45, 60, 72, 90, 120, or 180 degrees. In other embodiments, the electrodes 102 can be positioned approximately 5, 15, 25, 35, 40, 50, 55, 65, 70, 75, 80, 85, 95, 100, 105, 110, 115, 125, 130, 135, 140, 145, 150, 155, 160, 165, 170, 175 or any other suitable spacing from one another along the circumference 100c of the locator assembly 100.

In some embodiments, the electrodes 102 can be distributed in a somewhat circular, oval, cylindrical, or any suitable pattern about the locator assembly 100. In one embodiment, the electrodes 102 can be evenly spaced apart from one another along the longitudinal axis 100a and/or about the circumference 100c of the locator assembly 100. In alternative embodiments, the electrodes 102 can be spaced apart from one another along the longitudinal axis 100a and/or about the circumference of the locator assembly 100 in an uneven, asymmetrical, semi-random or random manner.

The communicator 104 is used by the locator assembly 100 for wireless communication between the locator assembly 110 and an external device 105 (e.g., a computing device). Data collected by the locator assembly 100 can be sent wirelessly via the communicator 104 to the external device 105. In other words, the communicator 104 is configured to allow communication between the locator assembly 100 and the external device 105. Alternatively, the communicator 104 can allow for wired communication between the locator assembly 100 and the external device 105.

The type of communicator 104 and/or the positioning of the communicator 104 can vary depending on the design requirements of the locator assembly 100. The communicator 104 can include any suitable wireless communications device, such as a radio frequency, Bluetooth®, low energy antenna, and/or any suitable antenna as non-limiting, non-exclusive examples. The communicator 104 can also include any suitable wired communication device, such as wire antennas, dipole antennas, monopole antennas, loop antennas, transmission line antennas, etc. In some embodiments, the communicator 104 can be positioned differently than what is specifically illustrated in FIG. 1A.

The external device 105 can communicate via the communicator 104 to enable (i) the transfer of data between the locator assembly 100 and the external device 105, (ii) the utilization of the memory of the external device 105 to increase processing speeds of the locator assembly 100, and/or (iii) the storage of data on the external device 105 following the transfer of the data from the locator assembly 100 to the external device 105. In some embodiments, the external device 105 can communicate with the communicator 104 to execute a set of processing instructions on the locator assembly 100. For example, the external device 105 can communicate via the communicator 104 to power the locator assembly 100 on or off.

The external device 105 can vary depending on the design requirements of the locator assembly 100. The connection between the communicator 104 and the external device 105 is merely demonstrative. The connection can indicate a wired and/or wireless connection between the locator assembly 100, the communicator 104, and/or the external device 105.

The controller 106 can control the components of the locator assembly 100. The controller 106 can vary depending on the design requirements of the locator assembly 100. In some embodiments, the controller 106 can be positioned differently than what is specifically illustrated in FIG. 1A.

The controller 106 can include (as non-limiting, non-exclusive examples) processors, microprocessors, diodes, capacitors, power storage elements, ASICs, sensors, image elements (e.g., CMOS, CCD imaging elements), amplifiers, A/D, and D/A converters, associated differential amplifiers, buffers, microprocessors, optical collectors, transducers including electro-mechanical transducers, piezoelectric actuators, light-emitting electronics which include LEDs, logic, memory, clock, and transistors including active matrix switching transistors, and combinations thereof. Components within electronic devices or devices are described herein and include those components described herein. A component can be one or more of any of the electronic devices described herein and/or may include a photodiode, LED, TUFT, electrode, semiconductor, other light-collecting/detecting components, transistor, contact pad capable of contacting a device component, thin-film devices, circuit elements, control elements, microprocessors, interconnects, contact pads, capacitors, resistors, inductors, a memory element, power storage element, antenna, logic element, buffer and/or other passive or active components. A component of the locator assembly 100 may be connected to one or more contact pads as known in the art, such as metal evaporation, wire bonding, application of solids or conductive pastes, and the like. The processor within the controller 106 can process and store data from each of the plurality of electrodes 102.

The routing layer 108 routes the components of the locator assembly 100 and/or the controller 106 to properly connect the components according to the design of the locator assembly 100 and/or the controller 106. The routing layer 108 can vary depending on the design requirements of the locator assembly 100 and/or the controller 106. In some embodiments, the routing layer 108 can be positioned differently than what is specifically illustrated in FIG. 1A. The routing layer 108 can include wiring, substrates, and/or other circuitry that are encased in a non-conductive dielectric material.

The battery 110 stores power and provides power to the various components of the locator assembly 100. The battery 110 can vary depending on the design requirements of the locator assembly 100. In some embodiments, the battery 110 can be positioned differently than what is specifically illustrated in FIG. 1A.

The battery 110 can be single-use/disposable, or it can be rechargeable. The battery 110 can be any suitable battery for use within the locator assembly 100. Non-limiting, non-exclusive examples of batteries 110 that can be used within the locator assembly 100 include alkaline, lithium, lithium-ion, lithium-iron-phosphate, lithium silicon, magnesium, mercury, mercury-oxide, silver-oxide, silver-zinc, zinc-air, zinc-carbon, zinc-chloride, lead, lead-acid gel, nickel-cadmium, nickel oxyhydroxide, nickel-metal hydride, nickel-zinc, and Absolyte® batteries. The battery 110 can also be a solid-state battery. The battery 110 can be any suitable size and/or shape for use within the locator assembly 100, such as the partial-cylinder shape illustrated in the embodiment shown in FIG. 1A.

In some embodiments, the battery 110 can be configured to power the locator assembly 100 for five years or more. In certain embodiments, the battery 110 can be configured to power the locator assembly 100 for less than five years. In various embodiments, the battery 110 can be wirelessly recharged. In another embodiment, the battery 110 can include a capacitor.

The device body 112 provides at least some structure for the locator assembly 100. The device body 112 can provide a substrate to secure various components of the locator assembly 100. The device body 112 can include a framework and/or a lattice structure for expansion and contraction. In some embodiments, when the framework in the device body 112 expands in circumference, a longitudinal length of the device body 112 does not expand. In other embodiments, when the framework in the device body 112 expands in circumference, the longitudinal length of the device body 112 expands.

In certain embodiments, when the framework in the device body 112 expands in circumference and/or longitudinal length, the electrodes 102, the communicator 104, the controller 106, the routing layer 108, and the battery 110 also expand in circumference and/or longitudinal length. Alternatively, in some such embodiments, when the framework in the device body 112 contract in circumference and/or longitudinal length, the electrodes 102, the communicator 104, the controller 106, the routing layer 108, and the battery 110 also contract in circumference and/or longitudinal length. The various components of the locator assembly 100 including the electrodes 102, the communicator 104, the controller 106, the routing layer 108, and the battery 110, can be formed by flexible and/or expandable materials.

The device body 112 can expand and contract as needed to deploy and extract the locator assembly 100 within various regions of the heart 101 and body of the patient. The device body 112 can vary depending on the design requirements of the locator assembly 100. In some embodiments, the device body 112 can be configured differently than what is specifically illustrated in FIG. 1A. The device body 112 can be any suitable structure known in the art that only allows expansion and contraction in circumference. The cross-sectional shape of the device body 112 in the contracted state and the expanded state can vary. Non-limiting, non-exclusive examples of the cross-sectional shape of the device body 112 include circular-shaped, oval-shaped, egg-shaped, pentagonal-shaped, hexagonal-shaped, heptagonal-shaped, octagonal-shaped, decagonal-shaped, or any suitable shape.

Figure 1B:
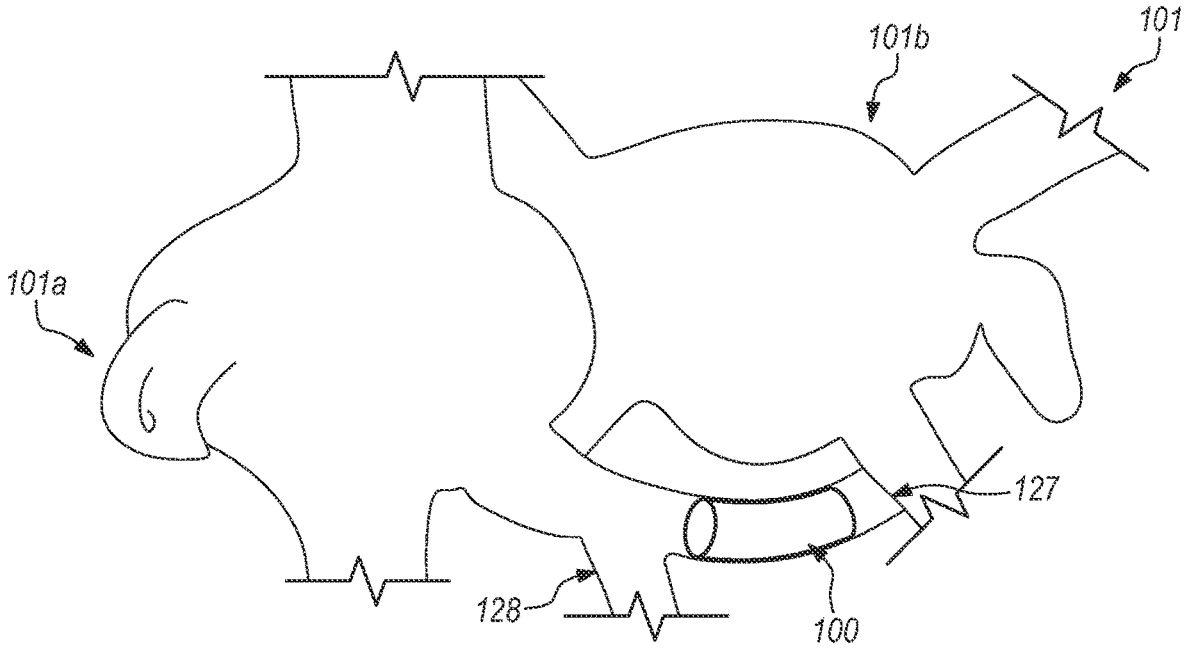
FIG. 1B is a simplified illustration of the heart and an embodiment of the locator assembly for locating the arrhythmogenic foci in or near the heart, the locator assembly being positioned within a portion of the heart.

FIG. 1B is a simplified illustration of the heart 101 and an embodiment of the locator assembly 100 positioned within the heart 101. The heart 101 includes a right atrium 101a and a left atrium 101b. As shown, the locator assembly 100 can be flexible to conform to portions of the heart 101 such as valves, veins, sinuses, etc. In particular, in the embodiment shown in FIG. 1B, the locator assembly 100 can be positioned in a coronary sinus 127 near a vena cordis media 128. However, it is understood that the locator assembly 100 can equally be positioned in other locations in or around the heart 101.

Figure 2A:
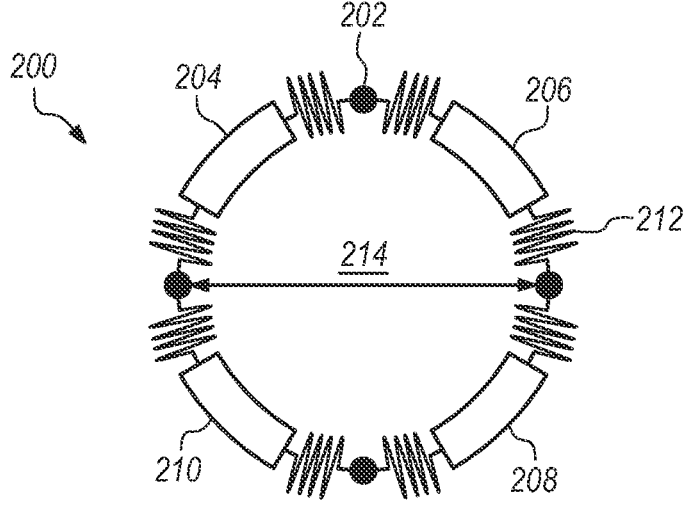
FIG. 2A is a simplified end view of an embodiment of the locator assembly, shown in a contracted state.

FIG. 2A is a simplified front elevation view of an embodiment of the locator assembly 200 being shown in a contracted state. As used herein, the "contracted state" is understood to mean the locator assembly 200 and/or the device body 212 is contracted or unexpanded. In the contracted state, the structures and/or components, including the electrodes 202, the communicator 204, the controller 206, the routing layer 208, and the battery 210 within the locator assembly 200, can be at least partially contracted. For example, in one embodiment of the locator assembly 200 shown in FIG. 2A, the device body 212 is in the contracted state when the framework in the device body 212 is contracted or unexpanded. For ease of understanding, the contracted state of the device body 212 in FIG. 2A is exaggerated to demonstrate the flexibility and/or contraction of the device body 212.

In the embodiment shown in FIG. 2A, the device body 212 is the only component shown to be in the contracted state. While in the contracted state, the locator assembly 200 has a contracted diameter 214. In some embodiments, the contracted diameter 214 illustrated and described herein can be between approximately 0.01 mm and 20.00 mm. In various non-exclusive embodiments, the contracted diameter 214 can be approximately 0.01 mm, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 6.1 mm, 6.2 mm, 6.3 mm, 6.4 mm, 6.5 mm, 6.6 mm, 6.7 mm, 6.8 mm, 6.9 mm, 7 mm, 7.1 mm, 7.2 mm, 7.3 mm, 7.4 mm, 7.5 mm, 7.6 mm, 7.7 mm, 7.8 mm, 7.9 mm, 8 mm, 8.1 mm, 8.2 mm, 8.3 mm, 8.4 mm, 8.5 mm, 8.6 mm, 8.7 mm, 8.8 mm, 8.9 mm, 9 mm, 9.1 mm, 9.2 mm, 9.3 mm, 9.4 mm, 9.5 mm, 9.6 mm, 9.7 mm, 9.8 mm, 9.9 mm, 10 mm, 10.1 mm, 10.2 mm, 10.3 mm, 10.4 mm, 10.5 mm, 10.6 mm, 10.7 mm, 10.8 mm, 10.9 mm, 11 mm, 11.1 mm, 11.2 mm, 11.3 mm, 11.4 mm, 11.5 mm, 11.6 mm, 11.7 mm, 11.8 mm, 11.9 mm, 12 mm, 12.1 mm, 12.2 mm, 12.3 mm, 12.4 mm, 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, 15 mm, 15.1 mm, 15.2 mm, 15.3 mm, 15.4 mm, 15.5 mm, 15.6 mm, 15.7 mm, 15.8 mm, 15.9 mm, 16 mm, 16.1 mm, 16.2 mm, 16.3 mm, 16.4 mm, 16.5 mm, 16.6 mm, 16.7 mm, 16.8 mm, 16.9 mm, 17 mm, 17.1 mm, 17.2 mm, 17.3 mm, 17.4 mm, 17.5 mm, 17.6 mm, 17.7 mm, 17.8 mm, 17.9 mm, 18 mm, 18.1 mm, 18.2 mm, 18.3 mm, 18.4 mm, 18.5 mm, 18.6 mm, 18.7 mm, 18.8 mm, 18.9 mm, 19 mm, 19.1 mm, 19.2 mm, 19.3 mm, 19.4 mm, 19.5 mm, 19.6 mm, 19.7 mm, 19.8 mm, 19.9 mm, or 20 mm. In other embodiments, the contracted diameter 214 can be less than approximately 0.01 mm or greater than approximately 20.00 mm.

Figure 2B:
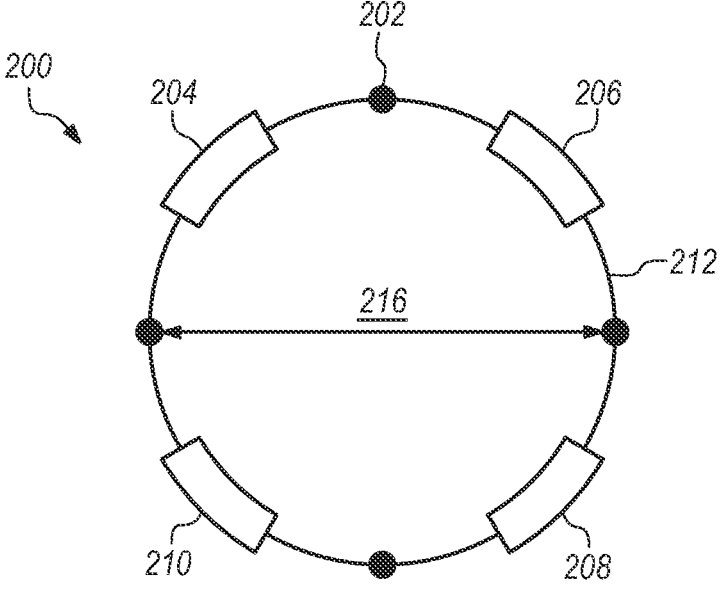
FIG. 2B is a simplified end view of an embodiment of the locator assembly, shown in an expanded state.

FIG. 2B is a simplified front elevation view of an embodiment of the locator assembly 200 being shown in an expanded state. As used herein, the "expanded state" is understood to mean the locator assembly 200 and/or the device body 212 is expanded outwardly from the contracted state so that the locator assembly 200 and/or the device body 212 has an increased circumference. The locator assembly 200 is movable between the contracted state and the expanded state.

While in the expanded state, the locator assembly 200 has an expanded diameter 216 that is greater than the contracted diameter 214. In some embodiments, the expanded diameter 216 illustrated and described herein can be between approximately 0.01 mm and 20.00 mm. In various non-exclusive embodiments, the expanded diameter 216 can be approximately 0.01 mm, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 6.1 mm, 6.2 mm, 6.3 mm, 6.4 mm, 6.5 mm, 6.6 mm, 6.7 mm, 6.8 mm, 6.9 mm, 7 mm, 7.1 mm, 7.2 mm, 7.3 mm, 7.4 mm, 7.5 mm, 7.6 mm, 7.7 mm, 7.8 mm, 7.9 mm, 8 mm, 8.1 mm, 8.2 mm, 8.3 mm, 8.4 mm, 8.5 mm, 8.6 mm, 8.7 mm, 8.8 mm, 8.9 mm, 9 mm, 9.1 mm, 9.2 mm, 9.3 mm, 9.4 mm, 9.5 mm, 9.6 mm, 9.7 mm, 9.8 mm, 9.9 mm, 10 mm, 10.1 mm, 10.2 mm, 10.3 mm, 10.4 mm, 10.5 mm, 10.6 mm, 10.7 mm, 10.8 mm, 10.9 mm, 11 mm, 11.1 mm, 11.2 mm, 11.3 mm, 11.4 mm, 11.5 mm, 11.6 mm, 11.7 mm, 11.8 mm, 11.9 mm, 12 mm, 12.1 mm, 12.2 mm, 12.3 mm, 12.4 mm, 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, 15 mm, 15.1 mm, 15.2 mm, 15.3 mm, 15.4 mm, 15.5 mm, 15.6 mm, 15.7 mm, 15.8 mm, 15.9 mm, 16 mm, 16.1 mm, 16.2 mm, 16.3 mm, 16.4 mm, 16.5 mm, 16.6 mm, 16.7 mm, 16.8 mm, 16.9 mm, 17 mm, 17.1 mm, 17.2 mm, 17.3 mm, 17.4 mm, 17.5 mm, 17.6 mm, 17.7 mm, 17.8 mm, 17.9 mm, 18 mm, 18.1 mm, 18.2 mm, 18.3 mm, 18.4 mm, 18.5 mm, 18.6 mm, 18.7 mm, 18.8 mm, 18.9 mm, 19 mm, 19.1 mm, 19.2 mm, 19.3 mm, 19.4 mm, 19.5 mm, 19.6 mm, 19.7 mm, 19.8 mm, 19.9 mm, or 20 mm. In other embodiments, the expanded diameter 216 can be less than approximately 0.01 mm or greater than approximately 20.00 mm.

In certain embodiments, a ratio of the expanded diameter 216 to the contracted diameter 214 for the locator assembly 200 herein can be between approximately 1:1 and 20:1. In some such non-exclusive embodiments, the ratio of the expanded diameter 216 to the contracted diameter 214 for the locator assembly 200 can be approximately 1:1, 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, 5:1, 5.1:1, 5.2:1, 5.3:1, 5.4:1, 5.5:1, 5.6:1, 5.7:1, 5.8:1, 5.9:1, 6:1, 6.1:1, 6.2:1, 6.3:1, 6.4:1, 6.5:1, 6.6:1, 6.7:1, 6.8:1, 6.9:1, 7:1, 7.1:1, 7.2:1, 7.3:1, 7.4:1, 7.5:1, 7.6:1, 7.7:1, 7.8:1, 7.9:1, 8:1, 8.1:1, 8.2:1, 8.3:1, 8.4:1, 8.5:1, 8.6:1, 8.7:1, 8.8:1, 8.9:1, 9:1, 9.1:1, 9.2:1, 9.3:1, 9.4:1, 9.5:1, 9.6:1, 9.7:1, 9.8:1, 9.9:1, 10:1, 10.1:1, 10.2:1, 10.3:1, 10.4:1, 10.5:1, 10.6:1, 10.7:1, 10.8:1, 10.9:1, 11:1, 11.1:1, 11.2:1, 11.3:1, 11.4:1, 11.5:1, 11.6:1, 11.7:1, 11.8:1, 11.9:1, 12:1, 12.1:1, 12.2:1, 12.3:1, 12.4:1, 12.5:1, 12.6:1, 12.7:1, 12.8:1, 12.9:1, 13:1, 13.1:1, 13.2:1, 13.3:1, 13.4:1, 13.5:1, 13.6:1, 13.7:1, 13.8:1, 13.9:1, 14:1, 14.1:1, 14.2:1, 14.3:1, 14.4:1, 14.5:1, 14.6:1, 14.7:1, 14.8:1, 14.9:1, 15:1, 15.1:1, 15.2:1, 15.3:1, 15.4:1, 15.5:1, 15.6:1, 15.7:1, 15.8:1, 15.9:1, 16:1, 16.1:1, 16.2:1, 16.3:1, 16.4:1, 16.5:1, 16.6:1, 16.7:1, 16.8:1, 16.9:1, 17:1, 17.1:1, 17.2:1, 17.3:1, 17.4:1, 17.5:1, 17.6:1, 17.7:1, 17.8:1, 17.9:1, 18:1, 18.1:1, 18.2:1, 18.3:1, 18.4:1, 18.5:1, 18.6:1, 18.7:1, 18.8:1, 18.9:1, 19:1, 19.1:1, 19.2:1, 19.3:1, 19.4:1, 19.5:1, 19.6:1, 19.7:1, 19.8:1, 19.9:1, 20:1, Alternatively, in some embodiments, the ratio of the expanded diameter 216 to the contracted diameter 214 for the locator assembly 200 can be greater than approximately 20:1 or less than approximately 1:1.

Figure 3:
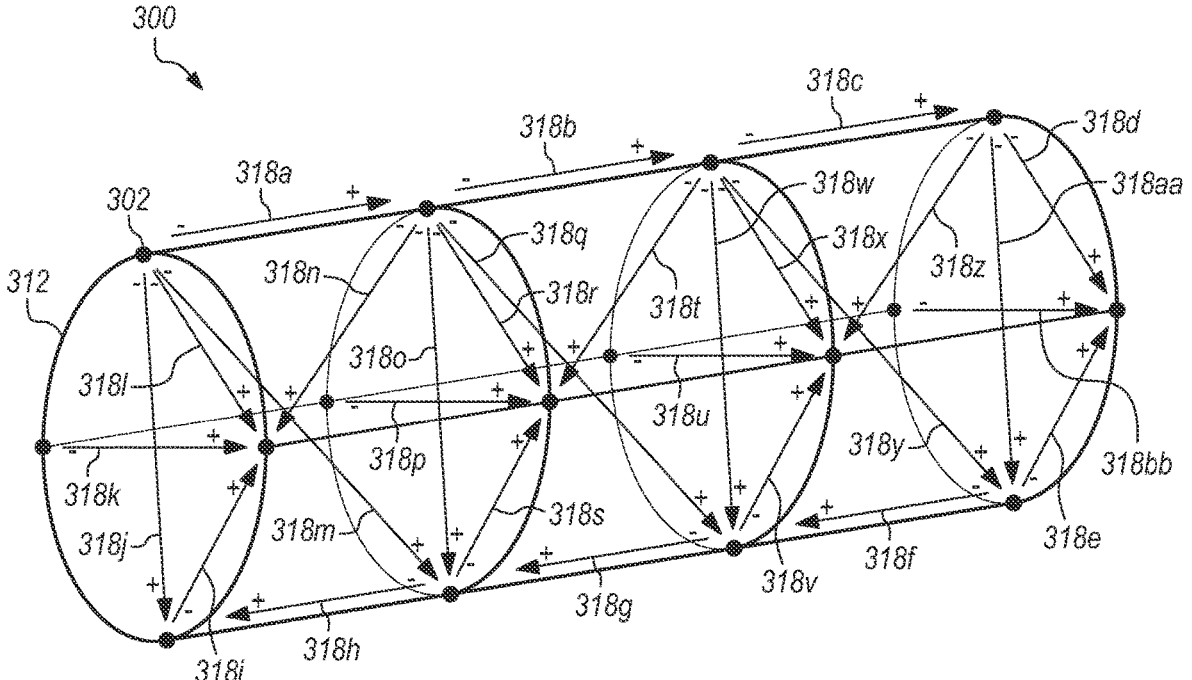
FIG. 3 is a simplified, partially transparent, perspective view of an embodiment of the locator assembly showing the bipolar relationships between pairs of electrodes within the locator assembly.

FIG. 3 is a simplified, partially transparent, perspective view of an embodiment of the locator assembly 300 illustrating the bipolar relationships between electrodes 302 within the locator assembly 300. In the embodiment illustrated in FIG. 3, the locator assembly 300 can include the device body 312 and a plurality of bipoles 318a-bb. The electrodes 302 can be bipolar electrodes having a negative polarity or positive polarity. In FIG. 3, the bipoles 318a-bb are illustrated as vectors that indicate bipoles of electrical current running across the locator assembly 300 from the electrode 302 having a negative polarity to the electrode 302 having a positive polarity. The electrode 302 having a negative polarity is referred to herein as a cathode, and the electrode 302 having a positive polarity is referred to herein as an anode.

The bipoles 318a-bb are formed between two electrical components (such as the anode and the cathode) with opposing polarities. In the bipoles 318a-bb, the electrical current runs across the locator assembly 300 between the electrical components of opposing polarities. The electrodes 302 can be excited by applying a current or a voltage to produce the bipoles 318*a-bb* between the anode and cathode. The current or the voltage can be applied to the electrodes 302 by the locator assembly 300 and/or the external device 105 (illustrated in FIG. 1).

The bipoles 318*a-bb* can vary depending on the design requirements of the locator assembly 300 and/or the electrodes 302. In some embodiments, such as illustrated in FIG. 3, a network of bipoles 318*a-bb*, including a plurality of anodes and cathodes, are arranged on the locator assembly 300. Multiple bipoles 318*a-bb* or multiple bipole networks can be arranged in any suitable portion of the locator assembly 300. The bipoles 318*a-bb* can be distributed about the longitudinal axis 100*a* (illustrated in FIG. 1) in a pattern, either in the longitudinal and/or circumferential directions or about or along any other suitable axis.

In some embodiments, the bipoles 318*a-bb* can be distributed in a somewhat circular, oval, cylindrical, or any suitable pattern about the locator assembly 300. In one embodiment, the bipoles 318*a-bb* can be evenly spaced apart from one another along the longitudinal axis 100*a* and/or about the circumference of the locator assembly 300. In alternative embodiments, the bipoles 318*a-bb* can be spaced apart from one another along the longitudinal axis 300*a* and/or about the circumference of the locator assembly 300 in an uneven, semi-random, or random manner. While 28 bipoles 318*a-bb* are displayed in the embodiment shown in FIG. 3, it is understood that more than 28 bipoles 318*a-bb* or less than 28 bipoles 318*a-bb* can be utilized by the locator assembly 300.

FIG. 4A is a simplified front elevation view of an embodiment of the locator assembly 400A. In particular, in the embodiment illustrated in FIG. 4A, the locator assembly 400A includes an inner layer 420A and an outer layer 422A. The inner layer 420A and the outer layer 422A can work in cooperation to substantially enclose and/or protect the components of the locator assembly 400A, including the electrode 402A, the communicator 404A, the controller 406A, the routing layer 408A, the battery 410A, and/or the device body 412A.

In other embodiments, the inner layer 420A can be coupled to the outer layer 422A to fully enclose the components of the locator assembly 400A, including the electrode 402A, the communicator 404A, the controller 406A, the routing layer 408A, the battery 410A, and/or the device body 412A. In certain embodiments, only one layer (e.g., the inner layer 420A or the outer layer 422A) can fully enclose the components of the locator assembly 400A, including the electrode 402A, the communicator 404A, the controller 406A, the routing layer 408A, the battery 410A, and/or the device body 412A.

The inner layer 420A and the outer layer 422A can cooperate to improve the protection of the patient and components of the locator assembly 400A upon the deployment of the locator assembly 400A within the patient. The inner layer 420A can provide a substantially uniform surface to improve the protection of a deployment balloon 526 (illustrated in FIG. 5) upon contact of the inner layer 420A with the deployment balloon 526. The outer layer 422A can reduce the likelihood of injury upon the contact of the outer layer 422A with one or more inner walls of portions of the heart 101 (illustrated FIG. 1B).

The inner layer 420A and/or the outer layer 422A can be in electrical communication with electrode 402A and the heart 101. The inner layer 420A and outer layer 422A can be at least partially formed from electrically conductive materials. In other embodiments, the inner layer 420A and/or the outer layer 422A can be formed with holes or apertures that are configured to allow the electrode 402A to come in direct contact with one or more inner walls of portions of the heart 101.

Figure 5A:
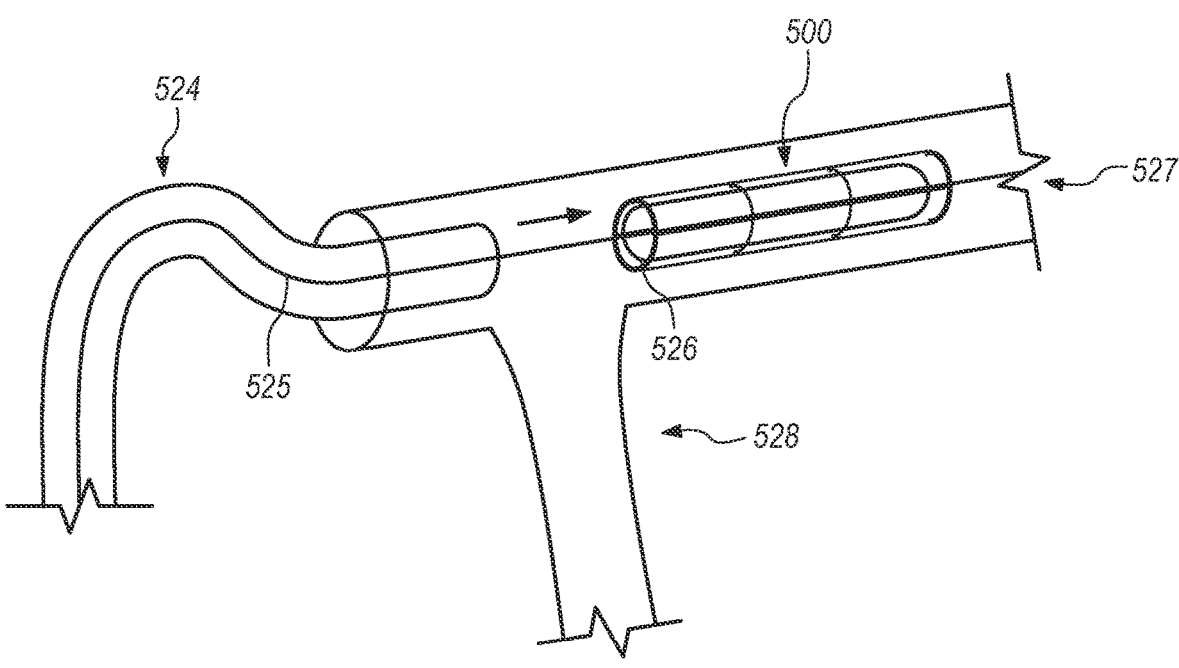
FIG. 5A is a simplified, partially transparent view of a portion of the heart, an embodiment of the locator assembly and an embodiment of a deployment catheter, the locator assembly being shown in the contracted state.
Figure 5B:
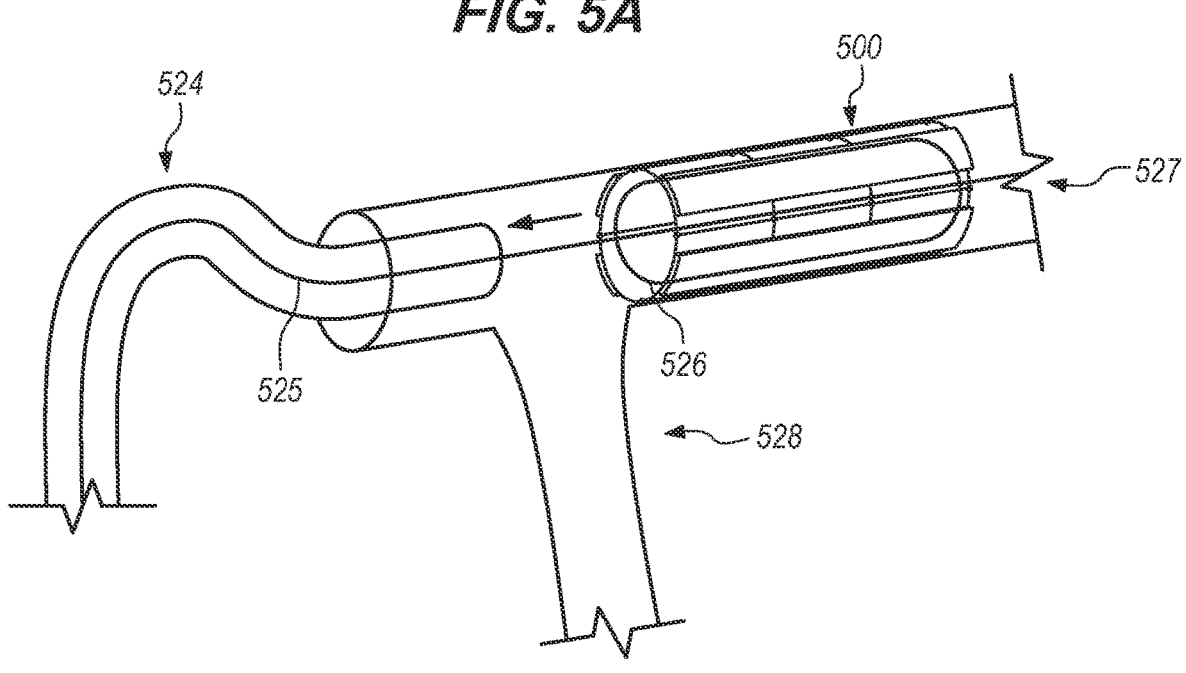
FIG. 5B is a simplified, partially transparent view of a portion of the heart, an embodiment of the locator assembly and an embodiment of the deployment catheter, the locator assembly being shown in the expanded state.

The inner layer 420A and/or the outer layer 422A can release an eluting drug over a period of time to counteract the pro-thrombotic and inflammatory potential of the locator assembly 400A at its deployed location (for example, one deployed location is depicted in FIGS. 5A-5B). In other embodiments, one or more drug-eluting layers (not shown in FIG. 4A) can be coupled to each of the inner layer 420A and/or the outer layer 422 Aso that the inner layer 420A and/or the outer layer 422A are positioned between the one or more drug-eluting layers and the device body 412A. In certain embodiments, the inner layer 420A and/or outer layer 422A can include multiple layers, including one or more drug-eluting layers. In various embodiments, other components of the locator assembly 400A (such as the device body 412A) can include an eluting drug and/or one or more drug-eluting layers.

Additionally, in the embodiment displayed in FIG. 4A, the locator assembly 400A is shown in an expanded state, where the locator assembly 400A has an expanded diameter 416. While the expanded state is shown in FIG. 4A, it is appreciated that the inner layer 420A and the outer layer 422A can be movable between the contracted state and the expanded state. The inner layer 420A can vary depending on the design requirements of the locator assembly 400A. In some embodiments, the inner layer 420A can be positioned differently than what is specifically illustrated in FIG. 4A.

The inner layer 420A can be formed from any suitable material. In certain embodiments, the inner layer 420A can be at least partially formed from a lubricious material and/or a continuous material. The inner layer 420A can be resilient, stretchable, and/or flexible. In some embodiments, the inner layer 420A can be at least partially formed from a metal, a plastic, a composite, a polymer, a coating, a biocompatible material, and/or a biodegradable material. Non-limiting, non-exclusive examples of suitable metals that can form the inner layer 420A include iron, magnesium, zinc, and their corresponding alloys. Non-limiting, non-exclusive examples of suitable polymers that can be used to form the inner layer 420A include polylactic acid, tyrosine polycarbonate, salicylic acid, poly-DL-lactide, and everolimus.

The inner layer 420A can include drugs to counteract the pro-thrombotic and inflammatory potential of the locator assembly 400A, such as immunosuppressive and antiproliferative drugs. Specific non-limiting, non-exclusive drugs usable within the inner layer 420A include sirolimus, paclitaxel, and everolimus. However, it is appreciated that any suitable, elutable drug can be utilized within the inner layer 420A.

The outer layer 422A can vary depending on the design requirements of the locator assembly 400A. In some embodiments, the outer layer 422A can be positioned differently than what is specifically illustrated in FIG. 4A. The outer layer 422A can be formed from any suitable material. In certain embodiments, the outer layer 422A can be at least partially formed from a lubricious material and/or a continuous material. The outer layer 422A can be resilient, stretchable, and/or flexible. In some embodiments, the outer layer 422A can be at least partially from a metal, a plastic, a composite, a polymer, a coating, a biocompatible material, and/or a biodegradable material. Non-limiting, non-exclusive examples of suitable metals that can form the outer layer 422A include iron, magnesium, zinc, and their corresponding alloys. Non-limiting, non-exclusive examples of suitable polymers that can be used to form the outer layer 422A include polylactic acid, tyrosine polycarbonate, salicylic acid, poly-DL-lactide, and everolimus.

The outer layer 422A can include drugs to counteract the pro-thrombotic and inflammatory potential of the locator assembly 400A, such as immunosuppressive and antiproliferative drugs. Specific non-limiting, non-exclusive drugs usable within the outer layer 422A include sirolimus, paclitaxel, and everolimus. However, it is appreciated that any suitable, elutable drug can be utilized within the outer layer 422A.

FIG. 4B is a simplified end view of yet another embodiment of the locator assembly 400B. In particular, in the embodiment illustrated in FIG. 4B, the locator assembly 400B includes an inner layer 420B and an outer layer 422B. The inner layer 420B and the outer layer 420B can work in cooperation to substantially enclose and/or protect the components of the locator assembly 400B, including the electrode 402B, the communicator 404B, the controller 406B, the routing layer 408B, the battery 410B, and/or the device body 412B. The locator assembly 400B, the electrode 402B, the communicator 404B, the controller 406B, the routing layer 408B, the battery 410B, the device body 412B, inner layer 420B, and/or the outer layer 420B can be substantially similar to the locator assembly 400A, the electrode 402A, the communicator 404A, the controller 406A, the routing layer 408A, the battery 410A, the device body 412A, inner layer 420A and/or the outer layer 420A described with respect to FIG. 4A and the other embodiments described herein.

The locator assembly 400B is movable between a locked state and an unlocked state. In the embodiment illustrated in FIG. 4B, the locator assembly 400B is shown in a locked state. In some embodiments, while the locator assembly 400B is in an unlocked state, the outer layer 422B can be separately deployable from the rest of the locator assembly 400B. In other embodiments, the outer layer 422B can remain deployed at a deployment location (e.g., the location displayed in FIGS. 5A-B, 6) while the rest of the locator assembly 400B is removed from the deployment location. A new locator assembly 400B can be deployed and engaged within the outer layer 422B at the deployment location. In certain embodiments, the locator assembly 400B can include a locking assembly 480.

The locking assembly 480 can facilitate the locking and/or separating of the outer layer 422B with the remainder of the locator assembly 400B and/or the device body 412B. For example, the locking assembly 480 enables locking and/or separation of the outer layer 422B from the remainder of the locator assembly 400B and/or the device body 412B by mechanical manipulation of the deployment catheter 524 (illustrated in FIG. 5). The deployment catheter 524 can lock and unlock the locking assembly 480 so that the locator assembly 400B is separately positionable with respect to the outer layer 422B. In other embodiments, the patient, the clinician, and/or the external device 105 (illustrated in FIG. 1) can lock and/or unlock the locking assembly 480 without the mechanical manipulation of the deployment catheter 524. For example, in some embodiments, the external device 105 can wirelessly transmit (e.g., via the communicator 404B) a locking command and/or an unlocking command to the locking assembly 480 in order to lock or unlock the locking assembly 480.

The locking assembly 480 can vary depending on the design requirements of the locator assembly 400 and/or the outer layer 422. It is understood that the locking assembly

480 can include additional components, systems, subsystems, and elements other than those specifically shown and/or described herein. Additionally, or alternatively, the locking assembly 480 can omit one or more of the components, systems, subsystems, and elements that are specifically shown and/or described herein. In some embodiments, the locking assembly 480 and the various components of the locking assembly 480 can be positioned in a different manner than what is specifically illustrated in FIG. 4B.

The locking assembly 480 can include a first locking mechanism 482 and a second locking mechanism 484. The first locking mechanism 482 and the second locking mechanism 484 lock and/or engage each other so that the outer layer 422B is secured to the locator assembly 400B and/or the device body 412B. The first locking mechanism 482 can be coupled to the device body 412B and/or any suitable component of the locator assembly 400B. The second locking mechanism 484 can be coupled to the outer layer 422B and/or any suitable component of the locator assembly 400B.

While the locking assembly 480 includes two locking mechanisms in FIG. 4B, it is appreciated that the locking assembly 480 can include any number of locking and/or engagement structures or elements that allow the locking and/or engagement of the outer layer 422B to the locator assembly 400B and/or the device body 412B. In some embodiments, as non-limiting, non-exclusive examples, the first locking mechanism 482 and the second locking mechanism 484 can include one or more of a male/female hookup assembly, a teeth/recess assembly, a tongue/groove assembly, a latch, an anchor, a coupling, an interlocking shoulder, a bolt, a cable, a clamp, a connector, a hook, a loop, a flange protrusion, a joint, a seam, a channel, a guide, a linkage, a track, and/or a tray. The first locking mechanism 482 and the second locking mechanism 484 have been simplified for ease of understanding.

FIG. 4C is a simplified end view of a portion of the embodiment of the locator assembly 400B shown in FIG. 4B. As shown in FIG. 4C, the locator assembly 400B including the electrode 402B, the communicator 404B, the controller 406B, the routing layer 408B, the battery 410B, the device body 412B, the inner layer 420B, and/or the first locking mechanism 482 can be selectively unlocked and/or detached from the outer layer 422B and/or the second locking mechanism 484.

FIG. 4D is a simplified end view of yet another portion of the embodiment of the locator assembly shown in FIG. 4B. As shown in FIG. 4D, the outer layer 422B and/or the second locking mechanism 484 can be selectively unlocked and/or detached from the electrode 402B, the communicator 404B, the controller 406B, the routing layer 408B, the battery 410B, the device body 412B, the inner layer 420B, and/or the first locking mechanism 482.

FIG. 5A is a simplified, transparent view of an embodiment of the locator assembly 500 and embodiments of a deployment catheter 524, a guidewire 525, and a balloon 526. As illustrated in FIG. 5A, the locator assembly 500 is positioned within the coronary sinus 527 of the heart 101 (illustrated in FIG. 1) near the vena cordis media 528.

The deployment catheter 524 deploys the locator assembly 500 in a portion of the heart 101. The deployment catheter 524 can deploy the locator assembly 500 in the same or similar manner as the deployment catheter 524 would deploy an expandable stent. The deployment catheter 524 can advance the locator assembly 500 to a target site within the coronary sinus 527. In some embodiments (such as the embodiment shown in FIGS. 5A-5B), the target site can be near a junction between the coronary sinus 527 and the vena cordis media 528. The target site illustrated in FIGS. 5A-5B is merely demonstrative, and it is appreciated that the locator assembly 500 can be deployed in any suitable position within the patient. The deployment catheter 524 can deploy the locator assembly 500 while the device is in the contracted state, the expanded state, or between states (in FIG. 5A, the locator assembly 500 is shown in a contracted state).

The deployment catheter 524 can vary depending on the design requirements of the locator assembly 500. It is understood that the deployment catheter 524 can include additional components, systems, subsystems, and elements other than those specifically shown and/or described herein. Additionally, or alternatively, the deployment catheter 524 can omit one or more of the components, systems, subsystems, and elements that are specifically shown and/or described herein. In particular, the deployment catheter 524 in FIG. 5A-5B has been simplified, and some elements of the deployment catheter 524 have been omitted for ease of understanding. In some embodiments, the deployment catheter 524 can be positioned differently than what is specifically illustrated in FIG. 5A-5B.

In some embodiments, the deployment catheter 524 can be a percutaneous transcatheter or any suitable catheter. The deployment catheter 524 can include a guidewire 525 and an inflatable balloon 526 (sometimes referred to herein simply as a "balloon"). The deployment catheter 524 can be configured to move over the guidewire 525.

The guidewire 525 can advance components through an opening of the deployment catheter 524 (such as the locator assembly 500 and/or the balloon 526). The guidewire 525 can be advanced simultaneously with the deployment catheter 524 within the body of the patient. The guidewire 525 can vary depending on the design requirements of the locator assembly 500 and/or the deployment catheter 524. In some embodiments, the guidewire 525 can be positioned differently than what is specifically illustrated in FIG. 5A-5B.

The balloon 526 can be coupled to the deployment catheter 524 and/or the guidewire 525. The balloon 526 can be inflatable to move the locator assembly 500 between the contracted and expanded states. The balloon 526 can be deflated and removed from the interior of the locator assembly 500 after the locator assembly 500 has been moved to the contracted state from the expanded state. The balloon 526 can also be deflated and removed from the interior of the locator assembly 500 when the locator assembly 500 is in between the contracted state and the expanded state.

The balloon 526 can vary depending on the design requirements of the locator assembly 500, the deployment catheter 524, and/or the guidewire 525. In some embodiments, the balloon 526 can be positioned differently than what is specifically illustrated in FIG. 5A-5B. The balloon 526 illustrated in FIGS. 5A-5B has been simplified for ease of understanding.

FIG. 5B is a simplified, transparent view of an embodiment of the locator assembly 500 and an embodiment of the deployment catheter 524, the guidewire 525, and the balloon 526. In the embodiment shown in FIG. 5B, the locator assembly 500 is positioned within the coronary sinus 526 of the heart 101 (illustrated in FIG. 1), and the locator assembly 500 is shown in an expanded state. As shown in FIG. 5B, the guidewire 525 can extract the balloon 526 from the interior of the locator assembly 500. The balloon 526 can deflate so that it can retract within the interior of the deployment catheter 524.

Figure 6:
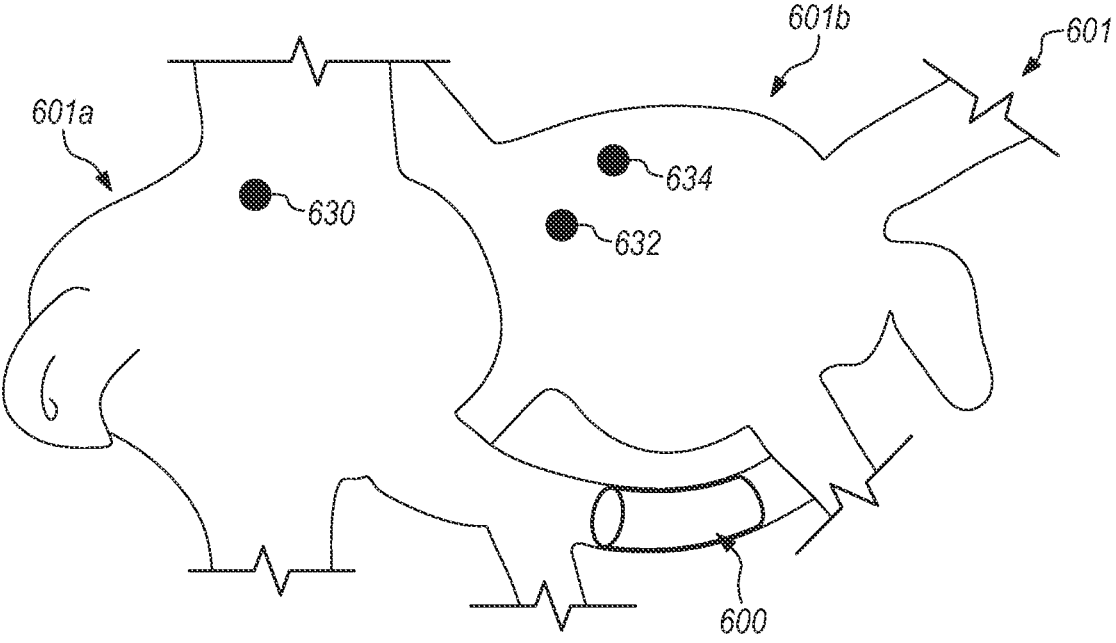
FIG. 6 is a simplified illustration of an embodiment of the locator assembly positioned within a portion of the heart, including a sinus rhythm foci, the arrhythmogenic foci, and a predicted foci in the heart.

FIG. 6 is a simplified illustration of the heart 601, including the right atrium 601a and the left atrium 601b, and an embodiment of the locator assembly 600 for determining the location of the arrhythmogenic foci 632 in or near the heart 601. In FIG. 6, the locator assembly 600 is positioned within a portion of the heart 601. For ease in understanding, FIG. 6 displays exemplar locations of a sinus rhythm foci 630, the arrhythmogenic foci 632, and a predicted foci 634 in the heart 601.

Figure 7:
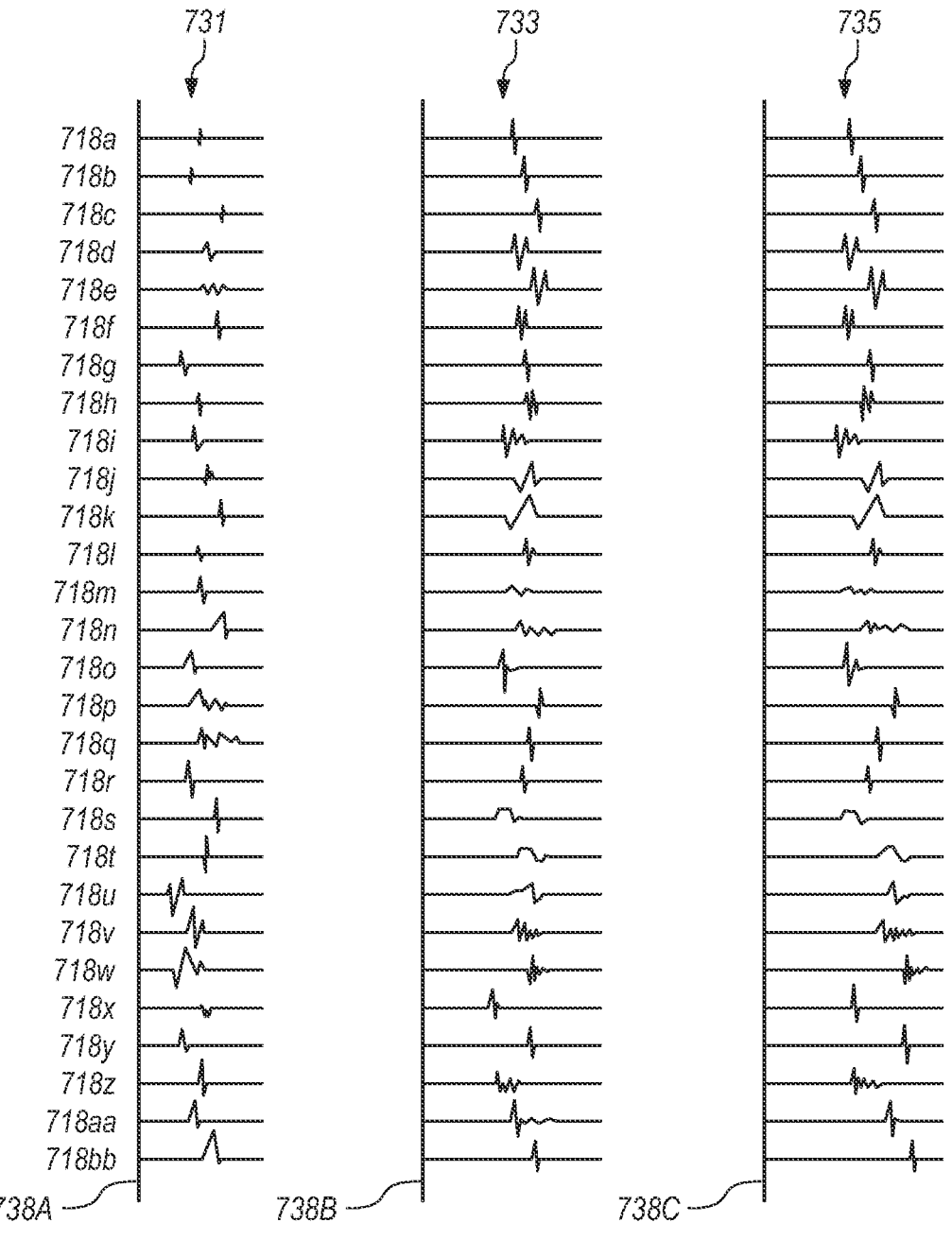
FIG. 7 is a simplified diagram illustrating a sinus signal array, a first signal array, and a second signal array generated during one embodiment of a method for locating the arrhythmogenic foci in or near the heart.

The sinus rhythm foci 630 is the focal point of a normal sinus rhythm of the patient. In particular, in some embodiments, the sinus rhythm foci 630 represents the origin of the electrical activation sequences of the normal sinus rhythm, such as from the sino-atrial node. One example of electrical activation sequence signal arrays recorded by the locator assembly 600 at the sinus rhythm foci 630 is illustrated in FIG. 7 in the left column.

The arrhythmogenic foci 632 illustrated in FIG. 6 is representative of one actual location of the focal point of an arrhythmia of the patient. It is appreciated that the arrhythmogenic foci 632 shown in FIG. 6 is merely demonstrative and/or representative, and can be located anywhere in and/or near the heart 601.

The predicted foci 634 in FIG. 6 represents the location of an artificial stimulation to determine and/or confirm whether the predicted foci 634 is the same or different than the actual arrhythmogenic foci 632. The predicted foci 634 and the arrhythmogenic foci 632 can be located at the same location (referred to herein as a "matched state") or different locations (referred to herein as an "unmatched state"), as described in greater detail herein.

The artificial stimulation can be generated using any suitable device known in the art, including ablation catheters, electrical stimulation and/or pace-makers, as non-exclusive examples. The artificial stimulation device can stimulate any suitable number of predicted foci 634 during one operation and/or insertion of the artificial stimulation device into the patient. In other words, the artificial stimulation device can test various predicted foci 634 locations in rapid succession.

FIG. 7 is a simplified diagram displaying electrical signal array data collected by the locator assembly 100 (illustrated in FIG. 1, for example). As shown in FIG. 7, the signal array data collected by the bipoles 318a-bb (illustrated in FIG. 3) is illustrated in descending rows as electrical signals 719a-bb. For example, FIG. 7 illustrates a sinus signal array 731 that is collected by the locator assembly 100 from the sinus rhythm foci 630 (illustrated in FIG. 6), a first signal array 733 that is collected by the locator assembly 100 from the arrhythmogenic foci 632 (illustrated in FIG. 6), and a second signal array 735 that is collected from the locator assembly 100 from the predicted foci 634 (illustrated in FIG. 6).

FIG. 7 illustrates the sinus signal array 731, the first signal array 733, and the second signal array 735 as displayed on a graphical user interface (GUI) of the external device 105 (illustrated in FIG. 1). It is understood that the actual display of the sinus signal array 731, the first signal array 733, and/or the second signal array 735 can appear differently than those shown in FIG. 7 and that the sinus signal array 731, the first signal array 733 and the second signal array 735 illustrated in FIG. 7 are provided as representative of one type of display for ease in understanding, and are not intended to be limiting in any manner. Any other suitable visual and/or auditory displays are contemplated and are intended to be included as alternative embodiments. Still alternatively, a haptic response can be incorporated into the display of the sinus signal array 731, the first signal array 733, and the second signal array 735.

The sinus signal array 731 illustrates the electrical activation sequence recorded by the locator assembly 100 implanted in the coronary sinus 527 (illustrated in FIG. 5) during the patient's normal sinus rhythm. In particular, the sinus signal array 731 is recorded by each of the bipoles 318a-bb to generate corresponding electrical signals 719a-bb in descending rows. For example, the bipole 318a receives the electrical signal 719a from the sinus rhythm foci 630 during the patient's normal sinus rhythm, which is then displayed in the first row of the sinus signal array 731. Each additional bipole 318b-318bb likewise receives the corresponding electrical signal 319b-319bb, which are likewise displayed in subsequent rows in the sinus signal array 731.

The sinus signal array 731 can be used for a comparative assessment of the different sequences between the two sources of a cardiac impulse origin. In particular, the sinus signal array 731 can represent the patient's electrical activation sequence of the sinus rhythm. The sinus signal array 731 can be used in comparison with the first signal array 733 and/or the second signal array 735.

In the embodiment illustrated in FIG. 7, the sinus signal array 731 includes an event initiation 738A represented as a vertical straight line in the sinus signal array 731. The event initiation 738A represents the onset of an actual event, such as an electrophysiological event including an electrical signal originating from the sinus rhythm foci (or sino-atrial node), for example. It is understood that the event initiation 738A represents a time (such as a $T_0$), after which electrical signals 719a-bb occur.

The first signal array 733 illustrates the electrical activation sequence located at the arrhythmogenic foci 632 and recorded by the locator assembly 100 implanted in the coronary sinus 527 during a clinical episode of atrial fibrillation of the patient. In particular, the first signal array 733 is recorded by each of the bipoles 318a-bb to generate corresponding electrical signals 719a-bb in descending rows. For example, the bipole 318a records the electrical activation sequence during a clinical episode of atrial fibrillation of the patient, and the corresponding electrical signal 719a is displayed in the first row of the first signal array 733. The first signal array 733 can be used in comparison with the second signal array 735, as provided in greater detail herein.

In the embodiment illustrated in FIG. 7, the first signal array 733 includes an event initiation 738B represented as a vertical straight line in the first signal array 733. The event initiation 738B represents the initiation of an actual event, such as an electrophysiological event including an electrical signal originating from the arrhythmogenic foci 632, for example. It is understood that the event initiation 738B represents a time (such as a $T_0$), after which electrical signals 719a-bb occur.

The second signal array 735 illustrates the electrical activation sequence taken at the predicted foci 634 and recorded by the locator assembly 100 implanted in the coronary sinus 527 during artificial stimulation of the patient at the predicted foci 634. In particular, the second signal array 735 is recorded by each of the bipoles 318a-bb to corresponding electrical signals 719a-bb in descending rows. For example, the bipole 318a records the electrical activation sequence during artificial stimulation of the patient at the predicted foci 634, and the corresponding electrical signal 719a is displayed on the first row in the second signal array 735. The second signal array 735 can be used in comparison with the first signal array 733, as provided in greater detail herein.

In the embodiment illustrated in FIG. 7, the second signal array 735 includes an event initiation 738C represented as a vertical straight line in the second signal array 735. The event initiation 738C represents the initiation of an actual event, such as an artificial stimulus that generates an electrical signal originating from the predicted foci 634, for example. It is understood that the event initiation 738C represents a time (such as a To), after which electrical signals 719a-bb occur.

Figure 8:
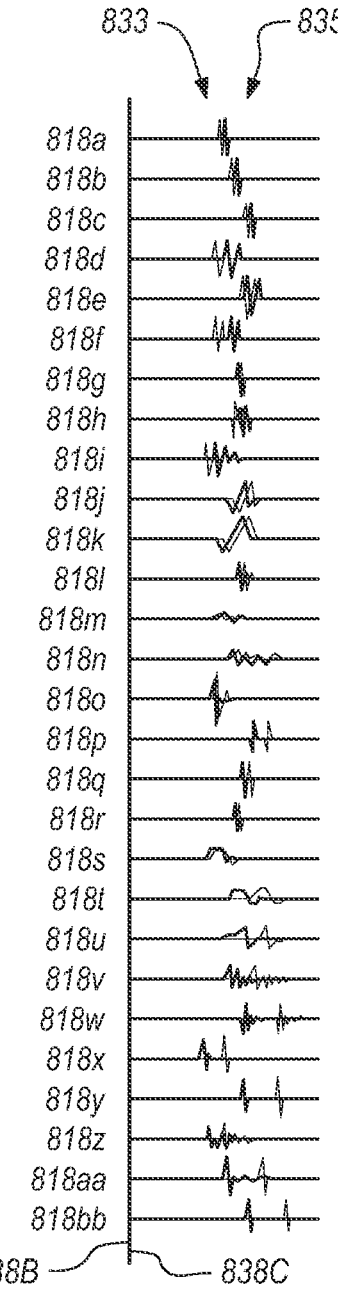
FIG. 8 is a simplified diagram illustrating a superimposition of the first signal array and the second signal array over one another generated during one embodiment of the method for locating the arrhythmogenic foci, the superimposition being shown in an unmatched state.

FIG. 8 is a simplified diagram illustrating a superimposition of the first signal array 833 and the second signal array 835 over one another generated during one embodiment of the method for locating the arrhythmogenic foci 632 (illustrated in FIG. 6). In FIG. 8, the superimposition is shown in an unmatched state. As shown in the embodiment displayed in FIG. 8, the electrical signals 819a-bb are recorded by the bipoles 318a-bb (illustrated in FIG. 3) in descending rows.

In the embodiment illustrated in FIG. 8, the first signal array 833 includes the event initiation 838B represented as a vertical straight line in the first signal array 833, and the second signal array 835 includes the event initiation 838C represented as a vertical straight line in the second signal array 835. In this embodiment, the event initiations 838B, 838C are aligned so a direct comparison between the first signal array 833 and the second signal array 835 can be achieved. Based on the superimposition displayed in FIG. 8, the clinician and/or the patient can determine and/or confirm that the arrhythmogenic foci 632 and the predicted foci 634 (illustrated in FIG. 6) are not in the same location as one another. In this embodiment, the signal arrays 833, 835 are not substantially similar or identical.

A negative sensory response can be incorporated into the locator assembly 100 (illustrated in FIG. 1), the deployment catheter 524 (illustrated in FIG. 5), and/or a related system in order to assist the clinician and/or the patient in determining that the arrhythmogenic foci 632 and the predicted foci 634 are not in the same location as one another (e.g., in the unmatched state). For example, in some embodiments, a negative haptic response can be incorporated into the display of the signal arrays 833, 835, or into a handle (not shown) of the deployment catheter 524. The negative haptic response can be a vibration or similar stimulation of touch and/or motion. The negative haptic response can be included on any suitable portion of the deployment catheter 524 or any suitable system and/or device. In other embodiments, a negative audio response can include a beep or any suitable audio feedback that is triggered when the superimposition is in the unmatched state. In certain embodiments, a negative visual response can include a red visual indicator and/or any suitable visual indication when the superimposition is in the unmatched state.

Figure 9:
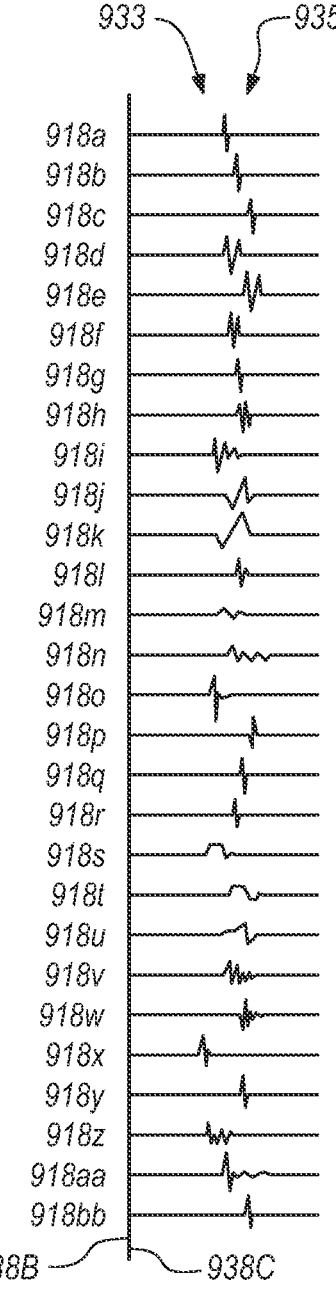
FIG. 9 is a simplified diagram illustrating a superimposition of the first signal array and the second signal array over one another generated during an embodiment of the method for determining the location of the arrhythmogenic foci, the superimposition being shown in a matched state.

FIG. 9 is a simplified diagram illustrating a superimposition of the first signal array 933 and the second signal array 935 over one another generated during an embodiment of the method for determining the location of the arrhythmogenic foci 632 (illustrated in FIG. 6), the superimposition being shown in a matched state. As shown in the embodiment displayed in FIG. 9, the electrical signals 919a-bb are recorded by the bipoles 318a-bb (illustrated in FIG. 3) in descending rows.

In the embodiment illustrated in FIG. 9, the first signal array 933 includes the event initiation 938B represented as a vertical straight line in the first signal array 933, and the second signal array 935 includes the event initiation 938C represented as a vertical straight line in the first signal array

935. In this embodiment, the event initiations 938B, 938C are aligned so a direct comparison between the first signal array 933 and the second signal array 935 can be achieved. Based on the superimposition displayed in FIG. 9, the clinician and/or the patient can determine and/or confirm that the arrhythmogenic foci 632 and the predicted foci 634 (illustrated in FIG. 6) are in the same location as one another because the signal arrays 833, 835, are substantially similar or identical.

A positive sensory response can be incorporated into the locator assembly 100 (illustrated in FIG. 1), the deployment catheter 524 (illustrated in FIG. 5), and/or a related system, in order to assist the clinician and/or the patient in determining that the arrhythmogenic foci 632 and the predicted foci 634 are in the same location as one another (e.g., in the matched state). For example, in some embodiments, a positive haptic response can be incorporated into the display of the signal arrays 833, 835, or into a handle (not shown) of the deployment catheter 524. The positive haptic response can be a vibration or similar stimulation of touch and/or motion. The positive haptic response can be included on any suitable portion of the deployment catheter 524 or any suitable system and/or device. In other embodiments, a positive audio response can include a beep or any suitable audio feedback that is triggered when the superimposition is in the matched state. In certain embodiments, a positive visual response can include a green visual indicator and/or any suitable visual indication when the superimposition is in the matched state.

FIG. 10 is a flow chart outlining one embodiment of a method for determining the location of arrhythmogenic foci in the heart. It is understood that the method pursuant to the disclosure herein can include greater or fewer steps than those shown and described relative to FIG. 10. The method can omit one or more steps illustrated in FIG. 10. The method can add additional steps not shown and described in FIG. 10, and still fall within the purview of the present invention. Further, the sequence of the steps can be varied from those shown and described relative to FIG. 10. The sequence of steps illustrated in FIG. 10 is not intended to limit the sequencing of steps in any manner.

In the embodiment illustrated in FIG. 10, at step 1040, a locator assembly is positioned within the heart. The locator assembly can include a plurality of electrodes that receive electrical signals from the heart. The locator assembly can be positioned within the heart using any suitable method known within the art, including those described herein. In some embodiments, the locator assembly can be positioned within a coronary sinus of the patient. However, other designs of locator assemblies can be utilized by the methods described herein. The locator assembly can include an expandable stent that is configured to be inserted into the heart.

At step 1042, a first signal array is generated from the electrical signals recorded by the locator assembly to determine the actual location of the arrhythmogenic foci. The locator assembly can use a plurality of electrodes arranged in bipolar relationships to receive the electrical signals. The electrical signals recorded by the plurality of electrodes can include atrial electrical activation signals. As used herein, the arrhythmogenic foci can also include any focal location within a human body associated with the development of perpetuation of atrial fibrillation.

At step 1044, the heart is artificially stimulated based on the actual location determined by the first signal array to generate a second signal array. The heart can be artificially stimulated by any suitable device known in the art. The second signal array can include the electrical activation sequence taken at the predicted foci and recorded by the locator assembly during a clinical episode of atrial fibrillation of the patient.

At step 1046, the second signal array is superimposed over the first signal array. The superimposition of the signal array data can be completed in the same and/or a similar manner as the embodiments illustrated in FIGS. 8-9. In some embodiments, the step of superimposing can be displayed on a graphical user interface (GUI) on an external device.

At step 1048, the superimposed signal arrays are compared. If the signal arrays match, the method proceeds to step 1050. If the signal arrays are not matched, the method restarts at step 1040.

At step 1050, the actual location of arrhythmogenic foci is confirmed, and the method for determining the location of arrhythmogenic foci in or near the heart is completed.

FIG. 11 is a flow chart outlining one embodiment of a method for determining the location of arrhythmogenic foci in the heart. It is understood that the method pursuant to the disclosure herein can include greater or fewer steps than those shown and described relative to FIG. 11. The method can omit one or more steps illustrated in FIG. 11. The method can add additional steps not shown and described in FIG. 11, and still fall within the purview of the present invention. Further, the sequence of the steps can be varied from those shown and described relative to FIG. 11. The sequence of steps illustrated in FIG. 11 is not intended to limit the sequencing of steps in any manner.

In the embodiment illustrated in FIG. 11, at step 1152, a locator assembly is positioned within the heart. The locator assembly can include a plurality of electrodes that receive electrical signals from the heart. However, other designs of locator assemblies can be used with the methods described herein.

At step 1154, a first signal array is generated from the electrical signals received by the locator assembly to determine an actual location of the arrhythmogenic foci.

At step 1156, the heart is artificially stimulated based on the actual location determined by the first signal array to generate a second signal array. The heart can be artificially stimulated by any suitable device known in the art.

At step 1158, the second signal array is superimposed over the first signal array. The superimposition of the signal data can be the same and/or similar to the embodiments illustrated in FIGS. 8-9. In some embodiments, the step of superimposing can be displayed on a graphical user interface (GUI) on an external device.

At step 1160, the superimposed signal arrays are compared. If the signal arrays match, the method proceeds to step 1162. If the signal arrays are not matched, the method restarts at step 1156.

At step 1162, the actual location of arrhythmogenic foci is confirmed, and the method for determining the location of arrhythmogenic foci in or near the heart is completed.

FIG. 12 is a flow chart outlining one embodiment of a method for determining the location of arrhythmogenic foci in the heart. It is understood that the method pursuant to the disclosure herein can include greater or fewer steps than those shown and described relative to FIG. 12. The method can omit one or more steps illustrated in FIG. 12. The method can add additional steps not shown and described in FIG. 12, and still fall within the purview of the present invention. Further, the sequence of the steps can be varied from those shown and described relative to FIG. 12. The sequence of steps illustrated in FIG. 12 is not intended to limit the sequencing of steps in any manner.

In the embodiment illustrated in FIG. 12, at step 1264, a locator assembly is positioned within the heart. The locator assembly can include a plurality of electrodes that receive electrical signals from the heart. However, other designs of locator assemblies can be used with the methods described herein.

At step 1266, a first signal array is generated from the electrical signals received by the locator assembly.

At step 1268, an actual location of the arrhythmogenic foci is determined.

At step 1270, the heart is artificially stimulated based on the actual location determined by the first signal array to generate a second signal array. The heart can be artificially stimulated by any suitable device known in the art.

At step 1272, at least one of the first and second signals array is processed with a processor.

At step 1274, the first signal array and the second signal array are superimposed.

At step 1276, the superimposed signal arrays are displayed on a graphical user interface. The superimposition of the signal data can be the same and/or similar to the embodiments illustrated in FIGS. 8-9.

At step 1278, the actual location of the arrhythmogenic foci is confirmed using the superimposed signal arrays.

The present technology provides a system, device, and method for determining the location of arrhythmogenic foci. The locator assembly can utilize protective materials such as inner/outer layers and can implement drug elution. The eluted drug is released over time to counteract the pro-thrombotic and inflammatory potential by the inflated locator assembly at its final location. Additionally, the present technology provides a safe housing between the inner and outer layer to host the various elements (integrated circuits, routing layers, battery, antenna) that compose the locator assembly.

It is appreciated that the system, device, and method provided herein address multiple potential issues with the performance, reliability, and proper usage of deliverable locator assemblies, in particular locator assemblies that utilize a plurality of bipolar electrodes to determine the location of the focal point of atrial fibrillation. Specific problems solved by the system, device, and method disclosed herein include:

1) The technology disclosed herein improves the deliverable locator technology to enable mapping of precipitating episodes of clinical atrial fibrillation during the patient's daily life;

2) The technology disclosed herein increases the accuracy of the determination of the location of the focal point of atrial fibrillation;

3) The technology disclosed herein reduces the time to determine the location of the focal point of atrial fibrillation;

4) The technology disclosed herein provides recharging capabilities for the locator assembly while implanted within the patient; and 5) The technology disclosed herein reduces the risk of thrombus formation and wall bleeding upon delivery and removal of the locator assembly.

It should be noted that, as used in this specification and the appended claims, the singular forms "a," "an," and "the" include plural referents unless the content and/or context clearly dictates otherwise. It should also be noted that the term "or" is generally employed in its sense, including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the detailed description provided herein. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of systems, devices, and methods for determining the location of arrhythmogenic foci have been illustrated and described herein, one or more features of any one embodiment can be combined with one or more features of one or more of the other embodiments, provided that such combination satisfies the intent of the present invention.

While a number of exemplary aspects and embodiments of the systems, devices, and methods for determining the location of arrhythmogenic foci have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope, and no limitations are intended to the details of construction or design herein shown.

What is claimed is:

1. A locator assembly for determining a location of an arrhythmogenic foci in or near a heart, the locator assembly having a longitudinal axis and a circumference, the locator assembly comprising:

an outer layer that is configured to be deployed into the heart of the patient;

a plurality of components that are couplable to the outer layer;

a plurality of electrodes that are couplable to the plurality of components and the outer layer, the plurality of electrodes being configured to receive electrical signals from the heart to determine the location of the arrhythmogenic foci; and an inner layer that is couplable to the plurality of components, the inner layer and the outer layer being configured to work cooperatively to protect the plurality of components, the inner layer and the plurality of components each being removable from the outer layer and the heart.

2. The locator assembly of claim 1 wherein the outer layer includes an eluting drug that is configured to counteract a pro-thrombotic and an inflammatory potential of the locator assembly.

3. The locator assembly of claim 1 wherein the plurality of components includes a communicator that is configured to allow communication between the locator assembly and an external device.

4. The locator assembly of claim 1 wherein the plurality of electrodes includes a plurality of anodes and cathodes that form a plurality of bipoles.

5. The locator assembly of claim 1 wherein the plurality of components further includes a routing layer that interconnects the plurality of electrodes, the routing layer being flexible.

6. The locator assembly of claim 1 wherein the plurality of electrodes includes at least 12 electrodes.

7. The locator assembly of claim 1 wherein the outer layer is configured to be permanently positioned within the heart of the patient.

8. The locator assembly of claim 1 wherein the plurality of components includes a controller that controls other components of the plurality of components.

9. The locator assembly of claim 1 wherein the outer layer is configured to be in electrical communication with the plurality of electrodes and the heart.

10. The locator assembly of claim 1 wherein the outer layer is at least partially formed from electrically conductive materials.

11. A locator assembly for determining a location of an arrhythmogenic foci in or near a heart, the locator assembly having a longitudinal axis and a circumference, the locator assembly comprising:

an outer layer that is configured to be deployed into the heart of the patient;

a plurality of components that are couplable to the outer layer;

a plurality of electrodes that are couplable to each of the plurality of components and the outer layer, the plurality of electrodes being configured to receive electrical signals from the heart to determine the location of the arrhythmogenic foci; and an inner layer that is couplable to the plurality of components, the inner layer and the plurality of components each being removable from the outer layer and the heart.

12. The locator assembly of claim 11 wherein the outer layer includes an eluting drug that is configured to counteract a pro-thrombotic and an inflammatory potential of the locator assembly.

13. The locator assembly of claim 11 wherein the plurality of components includes a communicator that is configured to allow communication between the locator assembly and an external device.

14. The locator assembly of claim 11 wherein the plurality of electrodes includes a plurality of anodes and cathodes that form a plurality of bipoles.

15. The locator assembly of claim 11 wherein the plurality of electrodes includes at least 12 electrodes.

16. The locator assembly of claim 11 wherein the outer layer is configured to be permanently positioned within the heart of the patient.

17. The locator assembly of claim 11 wherein the plurality of components includes a controller that controls other components of the plurality of components.

18. The locator assembly of claim 11 wherein the outer layer is configured to be in electrical communication with the plurality of electrodes and the heart.

19. The locator assembly of claim 11 wherein the outer layer is at least partially formed from electrically conductive materials.

20. A locator assembly for determining a location of an arrhythmogenic foci in or near a heart, the locator assembly having a longitudinal axis and a circumference, the locator assembly being configured to be permanently positioned within the heart, the locator assembly comprising:

an outer layer that is configured to be deployed into the heart of the patient;

a plurality of components that are couplable to the outer layer, the plurality of components including at least a plurality of electrodes that are configured to receive electrical signals from the heart to determine the location of the arrhythmogenic foci, the plurality of electrodes including a plurality of anodes and cathodes that form a plurality of bipoles, the plurality of components including a routing layer that interconnects the plurality of electrodes, the routing layer being flexible; and an inner layer that is coupled to the plurality of components, the inner layer and the outer layer being configured to work cooperatively to protect the plurality of components, the inner layer and the plurality of components each being removable from the outer layer and the heart.

* * * * *